(12) United States Patent
Nobis et al.

(10) Patent No.: US 8,403,926 B2
(45) Date of Patent: *Mar. 26, 2013

(54) MANUALLY ARTICULATING DEVICES

(75) Inventors: Rudolph H. Nobis, Mason, OH (US);
Sean P. Conlon, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1117 days.

This patent is subject to a terminal disclaimer.

(21) Appl. No.: 12/133,953

(22) Filed: Jun. 5, 2008

(65) Prior Publication Data

US 2009/0306658 A1    Dec. 10, 2009

(51) Int. Cl.
*A61B 18/14* (2006.01)
(52) U.S. Cl. ............................. 606/46; 606/39
(58) Field of Classification Search .......... 606/39, 606/46, 45, 50–52; 600/106, 137, 142
See application file for complete search history.

(56) References Cited

U.S. PATENT DOCUMENTS

| | | |
|---|---|---|
| 645,576 A | 3/1900 | Tesla |
| 649,621 A | 5/1900 | Tesla |
| 787,412 A | 4/1905 | Tesla |
| 1,127,948 A | 2/1915 | Wappler |
| 1,482,653 A | 2/1924 | Lilly |
| 1,625,602 A | 4/1927 | Gould et al. |
| 1,916,722 A | 7/1933 | Ende |
| 2,028,635 A | 1/1936 | Wappler |
| 2,031,682 A | 2/1936 | Wappler et al. |
| 2,113,246 A | 4/1938 | Wappler |
| 2,155,365 A | 4/1939 | Rankin |
| 2,191,858 A | 2/1940 | Moore |
| 2,196,620 A | 4/1940 | Attarian |
| 2,388,137 A | 10/1945 | Graumlich |
| 2,493,108 A | 1/1950 | Casey, Jr. |
| 2,504,152 A | 4/1950 | Riker et al. |
| 2,938,382 A | 5/1960 | De Graaf |

(Continued)

FOREIGN PATENT DOCUMENTS

| | | |
|---|---|---|
| AU | 666310 B2 | 2/1996 |
| DE | 3008120 A1 | 9/1980 |

(Continued)

OTHER PUBLICATIONS

Michael S. Kavic, M.D., "Natural Orifice Translumenal Endoscopic Surgery: "NOTES"", JSLS, vol. 10, pp. 133-134 (2006).

(Continued)

*Primary Examiner* — Michael Peffley
*Assistant Examiner* — Thomas Giuliani

(57) ABSTRACT

The device includes an elongate shaft having a distal end coupled to a proximal end of an articulation joint, and an actuation wire extending through the elongate shaft and the articulation joint. The device includes an end effector having a distal tip coupled to a distal end of the articulation joint and receiving therethrough a distal end of the actuation wire. The end effector includes a hook knife disposed adjacent the distal tip and having a proximal end connected to the distal end of the actuation wire. The actuation wire is translatable along a longitudinal axis of the elongate shaft to extend and retract the distal end of the hook knife relative to the distal tip of the end effector, and the articulation joint is laterally articulatable relative to the longitudinal axis of the elongate shaft to allow the end effector to be angularly oriented relative to the elongate shaft.

10 Claims, 14 Drawing Sheets

U.S. PATENT DOCUMENTS

| | | |
|---|---|---|
| 2,952,206 A | 9/1960 | Becksted |
| 3,069,195 A | 12/1962 | Buck |
| 3,070,088 A | 12/1962 | Brahos |
| 3,170,471 A | 2/1965 | Schnitzer |
| 3,435,824 A | 4/1969 | Gamponia |
| 3,470,876 A | 10/1969 | Barchilon |
| 3,595,239 A | 7/1971 | Petersen |
| 3,669,487 A | 6/1972 | Roberts et al. |
| 3,746,881 A | 7/1973 | Fitch et al. |
| 3,799,672 A | 3/1974 | Vurek |
| 3,854,473 A | 12/1974 | Matsuo |
| 3,946,740 A | 3/1976 | Bassett |
| 3,948,251 A | 4/1976 | Hosono |
| 3,994,301 A | 11/1976 | Agris |
| 4,011,872 A | 3/1977 | Komiya |
| 4,012,812 A | 3/1977 | Black |
| 4,085,743 A | 4/1978 | Yoon |
| 4,164,225 A | 8/1979 | Johnson et al. |
| 4,174,715 A | 11/1979 | Hasson |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,269,174 A | 5/1981 | Adair |
| 4,278,077 A | 7/1981 | Mizumoto |
| 4,285,344 A | 8/1981 | Marshall |
| 4,311,143 A | 1/1982 | Komiya |
| 4,329,980 A | 5/1982 | Terada |
| 4,396,021 A | 8/1983 | Baumgartner |
| 4,406,656 A | 9/1983 | Hattler et al. |
| 4,452,246 A | 6/1984 | Bader et al. |
| 4,461,281 A | 7/1984 | Carson |
| 4,491,132 A | 1/1985 | Aikins |
| 4,527,331 A | 7/1985 | Lasner et al. |
| 4,527,564 A | 7/1985 | Eguchi et al. |
| 4,538,594 A | 9/1985 | Boebel et al. |
| D281,104 S | 10/1985 | Davison |
| 4,569,347 A | 2/1986 | Frisbie |
| 4,580,551 A | 4/1986 | Siegmund et al. |
| 4,646,722 A | 3/1987 | Silverstein et al. |
| 4,653,476 A | 3/1987 | Bonnet |
| 4,655,219 A | 4/1987 | Petruzzi |
| 4,669,470 A | 6/1987 | Brandfield |
| 4,671,477 A | 6/1987 | Cullen |
| 4,677,982 A | 7/1987 | Llinas et al. |
| 4,685,447 A | 8/1987 | Iversen et al. |
| 4,711,240 A | 12/1987 | Goldwasser et al. |
| 4,712,545 A | 12/1987 | Honkanen |
| 4,721,116 A | 1/1988 | Schintgen et al. |
| 4,727,600 A | 2/1988 | Avakian |
| 4,733,662 A | 3/1988 | DeSatnick et al. |
| D295,894 S | 5/1988 | Sharkany et al. |
| 4,763,669 A | 8/1988 | Jaeger |
| 4,770,188 A | 9/1988 | Chikama |
| 4,815,450 A | 3/1989 | Patel |
| 4,823,794 A | 4/1989 | Pierce |
| 4,829,999 A | 5/1989 | Auth |
| 4,867,140 A | 9/1989 | Hovis et al. |
| 4,869,238 A | 9/1989 | Opie et al. |
| 4,869,459 A | 9/1989 | Bourne |
| 4,873,979 A | 10/1989 | Hanna |
| 4,880,015 A | 11/1989 | Nierman |
| 4,911,148 A | 3/1990 | Sosnowski et al. |
| 4,926,860 A | 5/1990 | Stice et al. |
| 4,938,214 A | 7/1990 | Specht et al. |
| 4,950,273 A | 8/1990 | Briggs |
| 4,950,285 A | 8/1990 | Wilk |
| 4,953,539 A | 9/1990 | Nakamura et al. |
| 4,960,133 A | 10/1990 | Hewson |
| 4,977,887 A | 12/1990 | Gouda |
| 4,979,950 A | 12/1990 | Transue et al. |
| 4,984,581 A | 1/1991 | Stice |
| 4,994,079 A | 2/1991 | Genese et al. |
| 5,007,917 A | 4/1991 | Evans |
| 5,010,876 A | 4/1991 | Henley et al. |
| 5,020,514 A | 6/1991 | Heckele |
| 5,020,535 A | 6/1991 | Parker et al. |
| 5,025,778 A | 6/1991 | Silverstein et al. |
| 5,033,169 A | 7/1991 | Bindon |
| 5,037,433 A | 8/1991 | Wilk et al. |
| 5,041,129 A | 8/1991 | Hayhurst et al. |
| 5,046,513 A | 9/1991 | Gatturna et al. |
| 5,050,585 A | 9/1991 | Takahashi |
| 5,052,372 A | 10/1991 | Shapiro |
| 5,065,516 A | 11/1991 | Dulebohn |
| 5,066,295 A | 11/1991 | Kozak et al. |
| 5,123,913 A | 6/1992 | Wilk et al. |
| 5,123,914 A | 6/1992 | Cope |
| 5,133,727 A | 7/1992 | Bales et al. |
| 5,147,374 A | 9/1992 | Fernandez |
| 5,174,300 A | 12/1992 | Bales et al. |
| 5,176,126 A | 1/1993 | Chikama |
| 5,190,050 A | 3/1993 | Nitzsche |
| 5,190,555 A | 3/1993 | Wetter et al. |
| 5,192,284 A | 3/1993 | Pleatman |
| 5,197,963 A | 3/1993 | Parins |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,217,003 A | 6/1993 | Wilk |
| 5,217,453 A | 6/1993 | Wilk |
| 5,219,357 A | 6/1993 | Honkanen et al. |
| 5,219,358 A | 6/1993 | Bendel et al. |
| 5,222,362 A | 6/1993 | Maus et al. |
| 5,222,965 A | 6/1993 | Haughton |
| 5,234,437 A | 8/1993 | Sepetka |
| 5,234,453 A | 8/1993 | Smith et al. |
| 5,235,964 A | 8/1993 | Abenaim |
| 5,242,456 A | 9/1993 | Nash et al. |
| 5,245,460 A | 9/1993 | Allen et al. |
| 5,246,424 A | 9/1993 | Wilk |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,275,614 A | 1/1994 | Haber et al. |
| 5,284,128 A | 2/1994 | Hart |
| 5,284,162 A | 2/1994 | Wilk |
| 5,287,845 A | 2/1994 | Faul et al. |
| 5,287,852 A | 2/1994 | Arkinstall |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,301,061 A | 4/1994 | Nakada et al. |
| 5,312,023 A | 5/1994 | Green et al. |
| 5,312,333 A | 5/1994 | Churinetz et al. |
| 5,312,351 A | 5/1994 | Gerrone |
| 5,312,416 A | 5/1994 | Spaeth et al. |
| 5,312,423 A | 5/1994 | Rosenbluth et al. |
| 5,318,589 A | 6/1994 | Lichtman |
| 5,320,636 A | 6/1994 | Slater |
| 5,324,261 A | 6/1994 | Amundson et al. |
| 5,325,845 A | 7/1994 | Adair |
| 5,330,471 A | 7/1994 | Eggers |
| 5,330,486 A | 7/1994 | Wilk |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,168 A | 8/1994 | Hemmer |
| 5,334,198 A | 8/1994 | Hart et al. |
| 5,342,396 A | 8/1994 | Cook |
| 5,344,428 A | 9/1994 | Griffiths |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,381 A | 10/1994 | Ensminger et al. |
| 5,356,408 A | 10/1994 | Rydell |
| 5,360,428 A | 11/1994 | Hutchinson, Jr. |
| 5,364,408 A | 11/1994 | Gordon |
| 5,364,410 A | 11/1994 | Failla et al. |
| 5,366,466 A | 11/1994 | Christian et al. |

| | | | | | | |
|---|---|---|---|---|---|---|
| 5,366,467 A | 11/1994 | Lynch et al. | | 5,582,617 A | 12/1996 | Klieman et al. |
| 5,368,605 A | 11/1994 | Miller, Jr. | | 5,584,845 A | 12/1996 | Hart |
| 5,370,647 A | 12/1994 | Graber et al. | | 5,591,179 A | 1/1997 | Edelstein |
| 5,370,679 A | 12/1994 | Atlee, III | | 5,593,420 A | 1/1997 | Eubanks, Jr. et al. |
| 5,374,273 A | 12/1994 | Nakao et al. | | 5,595,562 A | 1/1997 | Grier |
| 5,374,275 A | 12/1994 | Bradley et al. | | 5,597,378 A | 1/1997 | Jervis |
| 5,374,277 A | 12/1994 | Hassler | | 5,601,573 A | 2/1997 | Fogelberg et al. |
| 5,377,695 A | 1/1995 | An Haack | | 5,601,588 A | 2/1997 | Tonomura et al. |
| 5,383,877 A | 1/1995 | Clarke | | 5,604,531 A | 2/1997 | Iddan et al. |
| 5,383,888 A | 1/1995 | Zvenyatsky et al. | | 5,607,389 A | 3/1997 | Edwards et al. |
| 5,386,817 A | 2/1995 | Jones | | 5,607,406 A | 3/1997 | Hernandez et al. |
| 5,387,259 A | 2/1995 | Davidson | | 5,607,450 A | 3/1997 | Zvenyatsky et al. |
| 5,391,174 A | 2/1995 | Weston | | 5,609,601 A | 3/1997 | Kolesa et al. |
| 5,392,789 A | 2/1995 | Slater et al. | | 5,613,975 A | 3/1997 | Christy |
| 5,395,386 A | 3/1995 | Slater | | 5,618,303 A | 4/1997 | Marlow et al. |
| 5,401,248 A | 3/1995 | Bencini | | 5,620,415 A | 4/1997 | Lucey et al. |
| 5,403,328 A | 4/1995 | Shallman | | 5,624,399 A | 4/1997 | Ackerman |
| 5,403,342 A | 4/1995 | Tovey et al. | | 5,624,431 A | 4/1997 | Gerry et al. |
| 5,403,348 A | 4/1995 | Bonutti | | 5,626,578 A | 5/1997 | Tihon |
| 5,405,073 A | 4/1995 | Porter | | 5,628,732 A | 5/1997 | Antoon, Jr. et al. |
| 5,405,359 A | 4/1995 | Pierce | | 5,630,782 A | 5/1997 | Adair |
| 5,409,478 A | 4/1995 | Gerry et al. | | 5,643,283 A | 7/1997 | Younker |
| 5,417,699 A | 5/1995 | Klein et al. | | 5,643,292 A | 7/1997 | Hart |
| 5,423,821 A | 6/1995 | Pasque | | 5,643,294 A | 7/1997 | Tovey et al. |
| 5,433,721 A | 7/1995 | Hooven et al. | | 5,644,798 A | 7/1997 | Shah |
| 5,439,471 A | 8/1995 | Kerr | | 5,645,083 A | 7/1997 | Essig et al. |
| 5,439,478 A | 8/1995 | Palmer | | 5,645,565 A | 7/1997 | Rudd et al. |
| 5,441,059 A | 8/1995 | Dannan | | 5,649,372 A | 7/1997 | Souza |
| 5,441,494 A | 8/1995 | Ortiz | | 5,653,677 A | 8/1997 | Okada et al. |
| 5,441,499 A * | 8/1995 | Fritzsch .................... 606/45 | | 5,653,690 A | 8/1997 | Booth et al. |
| 5,443,463 A | 8/1995 | Stern et al. | | 5,653,722 A | 8/1997 | Kieturakis |
| 5,445,638 A | 8/1995 | Rydell et al. | | 5,657,755 A | 8/1997 | Desai |
| 5,445,648 A | 8/1995 | Cook | | 5,662,621 A | 9/1997 | Lafontaine |
| 5,449,021 A | 9/1995 | Chikama | | 5,662,663 A | 9/1997 | Shallman |
| 5,454,827 A | 10/1995 | Aust et al. | | 5,667,527 A | 9/1997 | Cook |
| 5,456,667 A | 10/1995 | Ham et al. | | 5,669,875 A | 9/1997 | van Eerdenburg |
| 5,456,684 A | 10/1995 | Schmidt et al. | | 5,681,324 A | 10/1997 | Kammerer et al. |
| 5,458,131 A | 10/1995 | Wilk | | 5,681,330 A | 10/1997 | Hughett et al. |
| 5,458,583 A | 10/1995 | McNeely et al. | | 5,685,820 A | 11/1997 | Riek et al. |
| 5,460,168 A | 10/1995 | Masubuchi et al. | | 5,690,606 A | 11/1997 | Slotman |
| 5,460,629 A | 10/1995 | Shlain et al. | | 5,690,656 A | 11/1997 | Cope et al. |
| 5,462,561 A | 10/1995 | Voda | | 5,690,660 A | 11/1997 | Kauker et al. |
| 5,465,731 A | 11/1995 | Bell et al. | | 5,695,448 A | 12/1997 | Kimura et al. |
| 5,467,763 A | 11/1995 | McMahon et al. | | 5,695,505 A | 12/1997 | Yoon |
| 5,468,250 A | 11/1995 | Paraschac et al. | | 5,695,511 A | 12/1997 | Cano et al. |
| 5,470,308 A | 11/1995 | Edwards et al. | | 5,700,275 A | 12/1997 | Bell et al. |
| 5,470,320 A | 11/1995 | Tiefenbrun et al. | | 5,702,438 A | 12/1997 | Avitall |
| 5,478,347 A | 12/1995 | Aranyi | | 5,704,892 A | 1/1998 | Adair |
| 5,480,404 A | 1/1996 | Kammerer et al. | | 5,709,708 A | 1/1998 | Thal |
| 5,482,054 A | 1/1996 | Slater et al. | | 5,716,326 A | 2/1998 | Dannan |
| 5,484,451 A | 1/1996 | Akopov et al. | | 5,728,094 A | 3/1998 | Edwards |
| 5,489,256 A | 2/1996 | Adair | | 5,730,740 A | 3/1998 | Wales et al. |
| 5,496,347 A | 3/1996 | Hashiguchi et al. | | 5,735,849 A | 4/1998 | Baden et al. |
| 5,499,990 A | 3/1996 | Schülken et al. | | 5,741,234 A | 4/1998 | Aboul-Hosn |
| 5,499,992 A | 3/1996 | Meade et al. | | 5,741,278 A | 4/1998 | Stevens |
| 5,501,692 A | 3/1996 | Riza | | 5,741,285 A | 4/1998 | McBrayer et al. |
| 5,503,616 A | 4/1996 | Jones | | 5,741,429 A | 4/1998 | Donadio, III et al. |
| 5,505,686 A | 4/1996 | Willis et al. | | 5,743,456 A | 4/1998 | Jones et al. |
| 5,507,755 A | 4/1996 | Gresl et al. | | 5,746,759 A | 5/1998 | Meade et al. |
| 5,511,564 A | 4/1996 | Wilk | | 5,749,826 A | 5/1998 | Faulkner |
| 5,514,157 A | 5/1996 | Nicholas et al. | | 5,749,881 A | 5/1998 | Sackier et al. |
| 5,518,501 A | 5/1996 | Oneda et al. | | 5,749,889 A | 5/1998 | Bacich et al. |
| 5,522,829 A | 6/1996 | Michalos | | 5,752,951 A | 5/1998 | Yanik |
| 5,522,830 A | 6/1996 | Aranyi | | 5,755,731 A | 5/1998 | Grinberg |
| 5,527,321 A | 6/1996 | Hinchliffe | | 5,766,167 A | 6/1998 | Eggers et al. |
| 5,536,248 A | 7/1996 | Weaver et al. | | 5,766,170 A | 6/1998 | Eggers |
| 5,538,509 A | 7/1996 | Dunlap et al. | | 5,766,205 A | 6/1998 | Zvenyatsky et al. |
| 5,540,648 A | 7/1996 | Yoon | | 5,769,849 A | 6/1998 | Eggers |
| 5,549,637 A | 8/1996 | Crainich | | 5,779,701 A | 7/1998 | McBrayer et al. |
| 5,554,151 A | 9/1996 | Hinchliffe | | 5,779,716 A | 7/1998 | Cano et al. |
| 5,555,883 A | 9/1996 | Avitall | | 5,779,727 A | 7/1998 | Orejola |
| 5,558,133 A | 9/1996 | Bortoli et al. | | 5,782,859 A | 7/1998 | Nicholas et al. |
| 5,562,693 A | 10/1996 | Devlin et al. | | 5,782,861 A | 7/1998 | Cragg et al. |
| 5,569,243 A | 10/1996 | Kortenbach et al. | | 5,782,866 A | 7/1998 | Wenstrom, Jr. |
| 5,569,298 A | 10/1996 | Schnell | | 5,791,022 A | 8/1998 | Bohman |
| 5,571,090 A | 11/1996 | Sherts | | 5,792,113 A | 8/1998 | Kramer et al. |
| 5,573,540 A | 11/1996 | Yoon | | 5,792,153 A | 8/1998 | Swain et al. |
| 5,578,030 A | 11/1996 | Levin | | 5,792,165 A | 8/1998 | Klieman et al. |
| 5,582,611 A | 12/1996 | Tsuruta et al. | | 5,797,835 A | 8/1998 | Green |

| Patent No. | Date | Inventor |
|---|---|---|
| 5,797,928 A | 8/1998 | Kogasaka |
| 5,797,939 A | 8/1998 | Yoon |
| 5,797,941 A | 8/1998 | Schulze et al. |
| 5,797,959 A | 8/1998 | Castro et al. |
| 5,803,903 A | 9/1998 | Athas et al. |
| 5,808,665 A | 9/1998 | Green |
| 5,810,806 A | 9/1998 | Ritchart et al. |
| 5,810,849 A | 9/1998 | Kontos |
| 5,810,865 A | 9/1998 | Koscher et al. |
| 5,810,876 A | 9/1998 | Kelleher |
| 5,810,877 A | 9/1998 | Roth et al. |
| 5,813,976 A | 9/1998 | Filipi et al. |
| 5,814,058 A | 9/1998 | Carlson et al. |
| 5,817,061 A | 10/1998 | Goodwin et al. |
| 5,817,107 A | 10/1998 | Schaller |
| 5,817,119 A | 10/1998 | Klieman et al. |
| 5,819,736 A | 10/1998 | Avny et al. |
| 5,823,947 A | 10/1998 | Yoon et al. |
| 5,824,071 A | 10/1998 | Nelson et al. |
| 5,827,276 A | 10/1998 | LeVeen et al. |
| 5,827,281 A | 10/1998 | Levin |
| 5,827,299 A | 10/1998 | Thomason et al. |
| 5,827,323 A | 10/1998 | Klieman et al. |
| 5,830,231 A | 11/1998 | Geiges, Jr. |
| 5,833,603 A | 11/1998 | Kovacs et al. |
| 5,833,700 A | 11/1998 | Fogelberg et al. |
| 5,833,703 A | 11/1998 | Manushakian |
| 5,836,960 A | 11/1998 | Kolesa et al. |
| 5,843,017 A * | 12/1998 | Yoon ................................ 604/22 |
| 5,843,121 A | 12/1998 | Yoon |
| 5,849,022 A | 12/1998 | Sakashita et al. |
| 5,853,374 A | 12/1998 | Hart et al. |
| 5,855,585 A | 1/1999 | Kontos |
| 5,860,913 A | 1/1999 | Yamaya et al. |
| 5,860,995 A | 1/1999 | Berkelaar |
| 5,868,762 A | 2/1999 | Cragg et al. |
| 5,876,411 A | 3/1999 | Kontos |
| 5,882,331 A | 3/1999 | Sasaki |
| 5,882,344 A | 3/1999 | Stouder, Jr. |
| 5,893,846 A | 4/1999 | Bales et al. |
| 5,893,874 A | 4/1999 | Bourque et al. |
| 5,893,875 A | 4/1999 | O'Connor et al. |
| 5,897,487 A | 4/1999 | Ouchi |
| 5,899,919 A | 5/1999 | Eubanks, Jr. et al. |
| 5,902,254 A | 5/1999 | Magram |
| 5,904,702 A | 5/1999 | Ek et al. |
| 5,908,420 A | 6/1999 | Parins et al. |
| 5,908,429 A | 6/1999 | Yoon |
| 5,911,737 A | 6/1999 | Lee et al. |
| 5,916,146 A | 6/1999 | Allotta et al. |
| 5,916,147 A | 6/1999 | Boury |
| 5,921,993 A | 7/1999 | Yoon |
| 5,921,997 A | 7/1999 | Fogelberg et al. |
| 5,922,008 A | 7/1999 | Gimpelson |
| 5,925,052 A | 7/1999 | Simmons |
| 5,928,255 A | 7/1999 | Meade et al. |
| 5,928,266 A | 7/1999 | Kontos |
| 5,936,536 A | 8/1999 | Morris |
| 5,944,718 A | 8/1999 | Austin et al. |
| 5,951,547 A | 9/1999 | Gough et al. |
| 5,951,549 A | 9/1999 | Richardson et al. |
| 5,954,720 A | 9/1999 | Wilson et al. |
| 5,954,731 A | 9/1999 | Yoon |
| 5,957,936 A | 9/1999 | Yoon et al. |
| 5,957,943 A | 9/1999 | Vaitekunas |
| 5,957,953 A | 9/1999 | DiPoto et al. |
| 5,964,782 A | 10/1999 | Lafontaine et al. |
| 5,971,995 A | 10/1999 | Rousseau |
| 5,972,002 A | 10/1999 | Bark et al. |
| 5,976,074 A | 11/1999 | Moriyama |
| 5,976,075 A | 11/1999 | Beane et al. |
| 5,976,130 A | 11/1999 | McBrayer et al. |
| 5,976,131 A | 11/1999 | Guglielmi et al. |
| 5,980,539 A | 11/1999 | Kontos |
| 5,980,556 A | 11/1999 | Giordano et al. |
| 5,984,938 A | 11/1999 | Yoon |
| 5,984,939 A | 11/1999 | Yoon |
| 5,984,950 A | 11/1999 | Cragg et al. |
| 5,989,182 A | 11/1999 | Hori et al. |
| 5,993,447 A | 11/1999 | Blewett et al. |
| 5,993,474 A | 11/1999 | Ouchi |
| 5,997,555 A | 12/1999 | Kontos |
| 6,001,120 A | 12/1999 | Levin |
| 6,004,269 A | 12/1999 | Crowley et al. |
| 6,004,330 A | 12/1999 | Middleman et al. |
| 6,007,566 A | 12/1999 | Wenstrom, Jr. |
| 6,010,515 A | 1/2000 | Swain et al. |
| 6,012,494 A | 1/2000 | Balazs |
| 6,017,356 A | 1/2000 | Frederick et al. |
| 6,019,770 A | 2/2000 | Christoudias |
| 6,024,708 A | 2/2000 | Bales et al. |
| 6,024,747 A | 2/2000 | Kontos |
| 6,027,522 A | 2/2000 | Palmer |
| 6,030,365 A | 2/2000 | Laufer |
| 6,030,384 A | 2/2000 | Nezhat |
| 6,030,634 A | 2/2000 | Wu et al. |
| 6,033,399 A | 3/2000 | Gines |
| 6,036,685 A | 3/2000 | Mueller |
| 6,053,927 A | 4/2000 | Hamas |
| 6,053,937 A | 4/2000 | Edwards et al. |
| 6,066,160 A | 5/2000 | Colvin et al. |
| 6,068,603 A | 5/2000 | Suzuki |
| 6,068,629 A | 5/2000 | Haissaguerre et al. |
| 6,071,233 A | 6/2000 | Ishikawa et al. |
| 6,074,408 A | 6/2000 | Freeman |
| 6,086,530 A | 7/2000 | Mack |
| 6,090,105 A | 7/2000 | Zepeda et al. |
| 6,090,108 A | 7/2000 | McBrayer et al. |
| 6,090,129 A | 7/2000 | Ouchi |
| 6,096,046 A | 8/2000 | Weiss |
| 6,102,926 A | 8/2000 | Tartaglia et al. |
| 6,106,473 A | 8/2000 | Violante et al. |
| 6,109,852 A | 8/2000 | Shahinpoor et al. |
| 6,110,154 A | 8/2000 | Shimomura et al. |
| 6,110,183 A | 8/2000 | Cope |
| 6,113,593 A | 9/2000 | Tu et al. |
| 6,117,144 A | 9/2000 | Nobles et al. |
| 6,117,158 A | 9/2000 | Measamer et al. |
| 6,139,555 A | 10/2000 | Hart et al. |
| 6,141,037 A | 10/2000 | Upton et al. |
| 6,146,391 A | 11/2000 | Cigaina |
| 6,148,222 A | 11/2000 | Ramsey, III |
| 6,149,653 A | 11/2000 | Deslauriers |
| 6,149,662 A | 11/2000 | Pugliesi et al. |
| 6,152,920 A | 11/2000 | Thompson et al. |
| 6,156,006 A | 12/2000 | Brosens et al. |
| 6,159,200 A | 12/2000 | Verdura et al. |
| 6,165,175 A | 12/2000 | Wampler et al. |
| 6,165,184 A | 12/2000 | Verdura et al. |
| 6,168,570 B1 | 1/2001 | Ferrera |
| 6,168,605 B1 | 1/2001 | Measamer et al. |
| 6,169,269 B1 | 1/2001 | Maynard |
| 6,170,130 B1 | 1/2001 | Hamilton et al. |
| 6,179,776 B1 | 1/2001 | Adams et al. |
| 6,179,832 B1 | 1/2001 | Jones et al. |
| 6,179,837 B1 | 1/2001 | Hooven |
| 6,183,420 B1 | 2/2001 | Douk et al. |
| 6,190,353 B1 | 2/2001 | Makower et al. |
| 6,190,384 B1 | 2/2001 | Ouchi |
| 6,190,399 B1 | 2/2001 | Palmer et al. |
| 6,203,533 B1 | 3/2001 | Ouchi |
| 6,206,872 B1 | 3/2001 | Lafond et al. |
| 6,206,877 B1 | 3/2001 | Kese et al. |
| 6,206,904 B1 | 3/2001 | Ouchi |
| 6,214,007 B1 | 4/2001 | Anderson |
| 6,216,043 B1 | 4/2001 | Swanson et al. |
| 6,228,096 B1 | 5/2001 | Marchand |
| 6,234,958 B1 | 5/2001 | Snoke et al. |
| 6,245,079 B1 | 6/2001 | Nobles et al. |
| 6,246,914 B1 | 6/2001 | de la Rama et al. |
| 6,258,064 B1 | 7/2001 | Smith et al. |
| 6,261,242 B1 | 7/2001 | Roberts et al. |
| 6,264,664 B1 | 7/2001 | Avellanet |
| 6,270,497 B1 | 8/2001 | Sekino et al. |
| 6,270,505 B1 | 8/2001 | Yoshida et al. |
| 6,277,136 B1 | 8/2001 | Bonutti |
| 6,283,963 B1 | 9/2001 | Regula |
| 6,293,909 B1 | 9/2001 | Chu et al. |

| | | |
|---|---|---|
| 6,293,952 B1 | 9/2001 | Brosens et al. |
| 6,296,630 B1 | 10/2001 | Altman et al. |
| 6,314,963 B1 | 11/2001 | Vaska et al. |
| 6,322,578 B1 | 11/2001 | Houle et al. |
| 6,325,534 B1 | 12/2001 | Hawley et al. |
| 6,326,177 B1 | 12/2001 | Schoenbach et al. |
| 6,328,730 B1 | 12/2001 | Harkrider, Jr. |
| 6,350,267 B1 | 2/2002 | Stefanchik |
| 6,350,278 B1 | 2/2002 | Lenker et al. |
| 6,352,503 B1 | 3/2002 | Matsui et al. |
| 6,352,543 B1 | 3/2002 | Cole |
| 6,355,013 B1 | 3/2002 | van Muiden |
| 6,355,035 B1 | 3/2002 | Manushakian |
| 6,361,534 B1 | 3/2002 | Chen et al. |
| 6,371,956 B1 | 4/2002 | Wilson et al. |
| 6,379,366 B1 | 4/2002 | Fleischman et al. |
| 6,383,195 B1 | 5/2002 | Richard |
| 6,383,197 B1 | 5/2002 | Conlon et al. |
| 6,387,671 B1 | 5/2002 | Rubinsky et al. |
| 6,391,029 B1 | 5/2002 | Hooven et al. |
| 6,398,708 B1 | 6/2002 | Hastings et al. |
| 6,402,735 B1 | 6/2002 | Langevin |
| 6,406,440 B1 | 6/2002 | Stefanchik |
| 6,409,727 B1 | 6/2002 | Bales et al. |
| 6,409,733 B1 | 6/2002 | Conlon et al. |
| 6,419,641 B1 | 7/2002 | Mark et al. |
| 6,427,089 B1 | 7/2002 | Knowlton |
| 6,431,500 B1 | 8/2002 | Jacobs et al. |
| 6,436,107 B1 | 8/2002 | Wang et al. |
| 6,443,970 B1 | 9/2002 | Schulze et al. |
| 6,443,988 B2 | 9/2002 | Felt et al. |
| 6,447,511 B1 | 9/2002 | Slater |
| 6,447,523 B1 | 9/2002 | Middleman et al. |
| 6,454,783 B1 | 9/2002 | Piskun |
| 6,454,785 B2 | 9/2002 | De Hoyos Garza |
| 6,458,076 B1 | 10/2002 | Pruitt |
| 6,464,701 B1 | 10/2002 | Hooven et al. |
| 6,464,702 B2 | 10/2002 | Schulze et al. |
| 6,470,218 B1 | 10/2002 | Behl |
| 6,475,104 B1 | 11/2002 | Lutz et al. |
| 6,485,411 B1 | 11/2002 | Konstorum et al. |
| 6,489,745 B1 | 12/2002 | Koreis |
| 6,491,626 B1 | 12/2002 | Stone et al. |
| 6,491,627 B1 | 12/2002 | Komi |
| 6,491,691 B1 | 12/2002 | Morley et al. |
| 6,493,590 B1 | 12/2002 | Wessman et al. |
| 6,494,893 B2 | 12/2002 | Dubrul et al. |
| 6,500,176 B1 | 12/2002 | Truckai et al. |
| 6,503,192 B1 | 1/2003 | Ouchi |
| 6,506,190 B1 | 1/2003 | Walshe |
| 6,508,827 B1 | 1/2003 | Manhes |
| 6,514,239 B2 | 2/2003 | Shimmura et al. |
| 6,520,954 B2 | 2/2003 | Ouchi |
| 6,527,782 B2 | 3/2003 | Hogg et al. |
| 6,530,922 B2 | 3/2003 | Cosman et al. |
| 6,537,200 B2 | 3/2003 | Leysieffer et al. |
| 6,543,456 B2 | 4/2003 | Freeman |
| 6,551,270 B1 | 4/2003 | Bimbo et al. |
| 6,554,766 B2 | 4/2003 | Maeda et al. |
| 6,554,829 B2 | 4/2003 | Schulze et al. |
| 6,558,384 B2 | 5/2003 | Mayenberger |
| 6,562,034 B2 | 5/2003 | Edwards et al. |
| 6,562,035 B1 | 5/2003 | Levin |
| 6,562,052 B2 | 5/2003 | Nobles et al. |
| 6,569,159 B1 * | 5/2003 | Edwards et al. ............ 606/41 |
| 6,572,629 B2 | 6/2003 | Kalloo et al. |
| 6,572,635 B1 | 6/2003 | Bonutti |
| 6,575,988 B2 | 6/2003 | Rousseau |
| 6,579,311 B1 | 6/2003 | Makower |
| 6,581,889 B2 | 6/2003 | Carpenter et al. |
| 6,585,642 B2 | 7/2003 | Christopher |
| 6,585,717 B1 | 7/2003 | Wittenberger et al. |
| 6,587,750 B2 | 7/2003 | Gerbi et al. |
| 6,592,559 B1 | 7/2003 | Pakter et al. |
| 6,592,603 B2 | 7/2003 | Lasner |
| 6,602,262 B2 | 8/2003 | Griego et al. |
| 6,605,105 B1 | 8/2003 | Cuschieri et al. |
| 6,610,072 B1 | 8/2003 | Christy et al. |
| 6,610,074 B2 | 8/2003 | Santilli |
| 6,613,068 B2 | 9/2003 | Ouchi |
| 6,620,193 B1 | 9/2003 | Lau et al. |
| 6,623,448 B2 | 9/2003 | Slater |
| 6,626,919 B1 | 9/2003 | Swanstrom |
| 6,632,229 B1 | 10/2003 | Yamanouchi |
| 6,638,275 B1 | 10/2003 | McGaffigan et al. |
| 6,638,286 B1 | 10/2003 | Burbank et al. |
| 6,645,225 B1 | 11/2003 | Atkinson |
| 6,652,521 B2 | 11/2003 | Schulze |
| 6,652,551 B1 | 11/2003 | Heiss |
| 6,656,194 B1 | 12/2003 | Gannoe et al. |
| 6,663,641 B1 | 12/2003 | Kovac et al. |
| 6,663,655 B2 | 12/2003 | Ginn et al. |
| 6,666,854 B1 | 12/2003 | Lange |
| 6,672,338 B1 | 1/2004 | Esashi et al. |
| 6,673,058 B1 | 1/2004 | Snow |
| 6,673,087 B1 | 1/2004 | Chang et al. |
| 6,673,092 B1 | 1/2004 | Bacher |
| 6,679,882 B1 | 1/2004 | Kornerup |
| 6,685,628 B2 | 2/2004 | Vu |
| 6,685,724 B1 | 2/2004 | Haluck |
| 6,692,445 B2 | 2/2004 | Roberts et al. |
| 6,692,462 B2 | 2/2004 | Mackenzie et al. |
| 6,699,180 B2 | 3/2004 | Kobayashi |
| 6,699,256 B1 | 3/2004 | Logan et al. |
| 6,699,263 B2 | 3/2004 | Cope |
| 6,706,018 B2 | 3/2004 | Westlund et al. |
| 6,708,066 B2 | 3/2004 | Herbst et al. |
| 6,709,445 B2 | 3/2004 | Boebel et al. |
| 6,716,226 B2 | 4/2004 | Sixto, Jr. et al. |
| 6,731,875 B1 | 5/2004 | Kartalopoulos |
| 6,736,822 B2 | 5/2004 | McClellan et al. |
| 6,740,030 B2 | 5/2004 | Martone et al. |
| 6,743,166 B2 | 6/2004 | Berci et al. |
| 6,743,239 B1 | 6/2004 | Kuehn et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,758,857 B2 | 7/2004 | Cioanta et al. |
| 6,761,685 B2 | 7/2004 | Adams et al. |
| 6,761,718 B2 | 7/2004 | Madsen |
| 6,773,434 B2 | 8/2004 | Ciarrocca |
| 6,776,787 B2 | 8/2004 | Phung et al. |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,382 B1 | 9/2004 | Hoffman |
| 6,786,864 B2 | 9/2004 | Matsuura et al. |
| 6,786,905 B2 | 9/2004 | Swanson et al. |
| 6,790,173 B2 | 9/2004 | Saadat et al. |
| 6,790,217 B2 | 9/2004 | Schulze et al. |
| 6,795,728 B2 | 9/2004 | Chornenky et al. |
| 6,800,056 B2 | 10/2004 | Tartaglia et al. |
| 6,808,491 B2 | 10/2004 | Kortenbach et al. |
| 6,817,974 B2 | 11/2004 | Cooper et al. |
| 6,818,007 B1 | 11/2004 | Dampney et al. |
| 6,824,548 B2 | 11/2004 | Smith et al. |
| 6,836,688 B2 | 12/2004 | Ingle et al. |
| 6,837,847 B2 | 1/2005 | Ewers et al. |
| 6,840,938 B1 | 1/2005 | Morley et al. |
| 6,843,794 B2 | 1/2005 | Sixto, Jr. et al. |
| 6,861,250 B1 | 3/2005 | Cole et al. |
| 6,866,627 B2 | 3/2005 | Nozue |
| 6,866,628 B2 | 3/2005 | Goodman et al. |
| 6,869,394 B2 | 3/2005 | Ishibiki |
| 6,878,106 B1 | 4/2005 | Herrmann |
| 6,878,110 B2 | 4/2005 | Yang et al. |
| 6,881,213 B2 | 4/2005 | Ryan et al. |
| 6,881,216 B2 | 4/2005 | Di Caprio et al. |
| 6,884,213 B2 | 4/2005 | Raz et al. |
| 6,887,255 B2 | 5/2005 | Shimm |
| 6,889,089 B2 | 5/2005 | Behl et al. |
| 6,896,683 B1 | 5/2005 | Gadberry et al. |
| 6,896,692 B2 | 5/2005 | Ginn et al. |
| 6,908,427 B2 | 6/2005 | Fleener et al. |
| 6,908,476 B2 | 6/2005 | Jud et al. |

| | | |
|---|---|---|
| 6,913,613 B2 | 7/2005 | Schwarz et al. |
| 6,916,284 B2 | 7/2005 | Moriyama |
| 6,918,871 B2 | 7/2005 | Schulze |
| 6,918,908 B2 | 7/2005 | Bonner et al. |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,936,003 B2 | 8/2005 | Iddan |
| 6,939,327 B2 | 9/2005 | Hall et al. |
| 6,942,613 B2 | 9/2005 | Ewers et al. |
| 6,944,490 B1 | 9/2005 | Chow |
| 6,945,472 B2 | 9/2005 | Wuttke et al. |
| 6,945,979 B2 | 9/2005 | Kortenbach et al. |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,984,203 B2 | 1/2006 | Tartaglia et al. |
| 6,984,205 B2 | 1/2006 | Gazdzinski |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,627 B2 | 1/2006 | Madhani et al. |
| 6,991,631 B2 | 1/2006 | Woloszko et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,001,341 B2 | 2/2006 | Gellman et al. |
| 7,008,375 B2 | 3/2006 | Weisel |
| 7,008,419 B2 | 3/2006 | Shadduck |
| 7,009,634 B2 | 3/2006 | Iddan et al. |
| 7,010,340 B2 | 3/2006 | Scarantino et al. |
| 7,020,531 B1 | 3/2006 | Colliou et al. |
| 7,025,580 B2 | 4/2006 | Heagy et al. |
| 7,029,435 B2 | 4/2006 | Nakao |
| 7,029,438 B2 | 4/2006 | Morin et al. |
| 7,029,450 B2 | 4/2006 | Gellman |
| 7,032,600 B2 | 4/2006 | Fukuda et al. |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,489 B2 | 5/2006 | Griego et al. |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,602 B2 | 7/2006 | Smith et al. |
| 7,076,305 B2 | 7/2006 | Imran et al. |
| 7,083,618 B2 | 8/2006 | Couture et al. |
| 7,083,620 B2 | 8/2006 | Jahns et al. |
| 7,083,629 B2 | 8/2006 | Weller et al. |
| 7,083,635 B2 | 8/2006 | Ginn |
| 7,087,071 B2 * | 8/2006 | Nicholas et al. ............ 606/206 |
| 7,088,923 B2 | 8/2006 | Haruyama |
| 7,090,673 B2 | 8/2006 | Dycus et al. |
| 7,090,683 B2 | 8/2006 | Brock et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,696 B2 | 9/2006 | Daniel et al. |
| 7,108,703 B2 | 9/2006 | Danitz et al. |
| 7,112,208 B2 | 9/2006 | Morris et al. |
| 7,115,092 B2 | 10/2006 | Park et al. |
| 7,115,124 B1 | 10/2006 | Xiao |
| 7,117,703 B2 | 10/2006 | Kato et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,128,708 B2 | 10/2006 | Saadat et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,150,097 B2 | 12/2006 | Sremcich et al. |
| 7,150,655 B2 | 12/2006 | Mastrototaro et al. |
| 7,150,750 B2 | 12/2006 | Damarati |
| 7,152,488 B2 | 12/2006 | Hedrich et al. |
| 7,153,321 B2 | 12/2006 | Andrews |
| 7,160,296 B2 | 1/2007 | Pearson et al. |
| 7,163,525 B2 | 1/2007 | Franer |
| 7,172,714 B2 | 2/2007 | Jacobson |
| 7,179,254 B2 | 2/2007 | Pendekanti et al. |
| 7,188,627 B2 | 3/2007 | Nelson et al. |
| 7,195,612 B2 | 3/2007 | Van Sloten et al. |
| 7,195,631 B2 | 3/2007 | Dumbauld |
| 7,204,820 B2 | 4/2007 | Akahoshi |
| 7,208,005 B2 | 4/2007 | Frecker et al. |
| 7,211,092 B2 | 5/2007 | Hughett |
| 7,220,227 B2 | 5/2007 | Sasaki et al. |
| 7,223,272 B2 | 5/2007 | Francere et al. |
| 7,229,438 B2 | 6/2007 | Young |
| 7,232,414 B2 | 6/2007 | Gonzalez |
| 7,232,445 B2 | 6/2007 | Kortenbach et al. |
| 7,235,089 B1 | 6/2007 | McGuckin, Jr. |
| 7,241,290 B2 | 7/2007 | Doyle et al. |
| 7,244,228 B2 | 7/2007 | Lubowski |
| 7,250,027 B2 | 7/2007 | Barry |
| 7,252,660 B2 | 8/2007 | Kunz |
| 7,255,675 B2 | 8/2007 | Gertner et al. |
| 7,270,663 B2 | 9/2007 | Nakao |
| 7,291,127 B2 | 11/2007 | Eidenschink |
| 7,294,139 B1 | 11/2007 | Gengler |
| 7,301,250 B2 | 11/2007 | Cassel |
| 7,306,597 B2 | 12/2007 | Manzo |
| 7,308,828 B2 | 12/2007 | Hashimoto |
| 7,318,802 B2 | 1/2008 | Suzuki et al. |
| 7,320,695 B2 | 1/2008 | Carroll |
| 7,322,934 B2 | 1/2008 | Miyake et al. |
| 7,323,006 B2 | 1/2008 | Andreas et al. |
| 7,329,256 B2 | 2/2008 | Johnson et al. |
| 7,329,257 B2 | 2/2008 | Kanehira et al. |
| 7,329,383 B2 | 2/2008 | Stinson |
| 7,344,536 B1 | 3/2008 | Lunsford et al. |
| 7,352,387 B2 | 4/2008 | Yamamoto |
| 7,364,582 B2 | 4/2008 | Lee |
| 7,371,215 B2 | 5/2008 | Colliou et al. |
| 7,381,216 B2 | 6/2008 | Buzzard et al. |
| 7,390,324 B2 | 6/2008 | Whalen et al. |
| 7,393,322 B2 | 7/2008 | Wenchell |
| 7,402,162 B2 | 7/2008 | Ouchi |
| 7,404,791 B2 | 7/2008 | Linares et al. |
| 7,410,483 B2 | 8/2008 | Danitz et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,435,229 B2 | 10/2008 | Wolf |
| 7,435,257 B2 | 10/2008 | Lashinski et al. |
| 7,452,327 B2 | 11/2008 | Durgin et al. |
| 7,455,208 B2 | 11/2008 | Wales et al. |
| 7,468,066 B2 | 12/2008 | Vargas et al. |
| 7,476,237 B2 | 1/2009 | Taniguchi et al. |
| 7,488,295 B2 | 2/2009 | Burbank et al. |
| 7,494,499 B2 | 2/2009 | Nagase et al. |
| 7,497,867 B2 | 3/2009 | Lasner et al. |
| 7,498,950 B1 | 3/2009 | Ertas et al. |
| 7,507,200 B2 | 3/2009 | Okada |
| 7,510,107 B2 | 3/2009 | Timm et al. |
| 7,511,733 B2 | 3/2009 | Takizawa et al. |
| 7,515,953 B2 | 4/2009 | Madar et al. |

| | | |
|---|---|---|
| 7,520,876 B2 | 4/2009 | Ressemann et al. |
| 7,524,281 B2 | 4/2009 | Chu et al. |
| 7,524,302 B2 | 4/2009 | Tower |
| 7,534,228 B2 | 5/2009 | Williams |
| 7,540,872 B2 | 6/2009 | Schechter et al. |
| 7,542,807 B2 | 6/2009 | Bertolero et al. |
| 7,544,203 B2 | 6/2009 | Chin et al. |
| 7,548,040 B2 | 6/2009 | Lee et al. |
| 7,549,564 B2 | 6/2009 | Boudreaux |
| 7,549,998 B2 | 6/2009 | Braun |
| 7,553,278 B2 | 6/2009 | Kucklick |
| 7,553,298 B2 | 6/2009 | Hunt et al. |
| 7,559,452 B2 | 7/2009 | Wales et al. |
| 7,559,887 B2 | 7/2009 | Dannan |
| 7,559,916 B2 | 7/2009 | Smith et al. |
| 7,560,006 B2 | 7/2009 | Rakos et al. |
| 7,561,907 B2 | 7/2009 | Fuimaono et al. |
| 7,561,916 B2 | 7/2009 | Hunt et al. |
| 7,566,334 B2 | 7/2009 | Christian et al. |
| 7,575,144 B2 | 8/2009 | Ortiz et al. |
| 7,575,548 B2 | 8/2009 | Takemoto et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,588,557 B2 | 9/2009 | Nakao |
| 7,597,229 B2 | 10/2009 | Boudreaux et al. |
| 7,604,150 B2 | 10/2009 | Boudreaux |
| 7,608,083 B2 | 10/2009 | Lee et al. |
| 7,618,398 B2 | 11/2009 | Holman et al. |
| 7,632,250 B2 | 12/2009 | Smith et al. |
| 7,635,373 B2 | 12/2009 | Ortiz |
| 7,637,903 B2 | 12/2009 | Lentz et al. |
| 7,650,742 B2 | 1/2010 | Ushijima |
| 7,651,483 B2 | 1/2010 | Byrum et al. |
| 7,651,509 B2 | 1/2010 | Bojarski et al. |
| 7,654,431 B2 | 2/2010 | Hueil et al. |
| 7,662,089 B2 | 2/2010 | Okada et al. |
| 7,666,180 B2 | 2/2010 | Holsten et al. |
| 7,666,203 B2 | 2/2010 | Chanduszko et al. |
| 7,674,259 B2 | 3/2010 | Shadduck |
| 7,678,043 B2 | 3/2010 | Gilad |
| 7,684,599 B2 | 3/2010 | Horn et al. |
| 7,686,826 B2 | 3/2010 | Lee et al. |
| 7,697,970 B2 | 4/2010 | Uchiyama et al. |
| 7,699,835 B2 | 4/2010 | Lee et al. |
| 7,699,864 B2 | 4/2010 | Kick et al. |
| 7,713,189 B2 | 5/2010 | Hanke |
| 7,713,270 B2 | 5/2010 | Suzuki |
| 7,736,374 B2 | 6/2010 | Vaughan et al. |
| 7,744,615 B2 | 6/2010 | Couture |
| 7,753,933 B2 | 7/2010 | Ginn et al. |
| 7,758,577 B2 | 7/2010 | Nobis et al. |
| 7,762,949 B2 | 7/2010 | Nakao |
| 7,762,998 B2 | 7/2010 | Birk et al. |
| 7,763,012 B2 | 7/2010 | Petrick et al. |
| 7,771,416 B2 | 8/2010 | Spivey et al. |
| 7,780,683 B2 | 8/2010 | Roue et al. |
| 7,780,691 B2 | 8/2010 | Stefanchik |
| 7,784,663 B2 | 8/2010 | Shelton, IV |
| 7,794,409 B2 | 9/2010 | Damarati |
| 7,794,475 B2 | 9/2010 | Hess et al. |
| 7,798,386 B2 | 9/2010 | Schall et al. |
| 7,828,186 B2 | 11/2010 | Wales |
| 7,837,615 B2 | 11/2010 | Le et al. |
| 7,842,028 B2 | 11/2010 | Lee |
| 7,842,068 B2 | 11/2010 | Ginn |
| 7,846,171 B2 | 12/2010 | Kullas et al. |
| 7,850,660 B2 | 12/2010 | Uth et al. |
| 7,857,183 B2 | 12/2010 | Shelton, IV |
| 7,862,546 B2 | 1/2011 | Conlon et al. |
| 7,867,216 B2 | 1/2011 | Wahr et al. |
| 7,879,004 B2 | 2/2011 | Seibel et al. |
| 7,892,220 B2 | 2/2011 | Faller et al. |
| 7,896,887 B2 | 3/2011 | Rimbaugh et al. |
| 7,905,828 B2 | 3/2011 | Brock et al. |
| 7,909,809 B2 | 3/2011 | Scopton et al. |
| 7,914,513 B2 | 3/2011 | Voorhees, Jr. |
| 7,918,869 B2 | 4/2011 | Saadat et al. |
| 7,931,624 B2 | 4/2011 | Smith et al. |
| 7,945,332 B2 | 5/2011 | Schechter |
| 7,947,000 B2 | 5/2011 | Vargas et al. |
| 7,953,326 B2 | 5/2011 | Farr et al. |
| 7,955,298 B2 | 6/2011 | Carroll et al. |
| 7,963,975 B2 | 6/2011 | Criscuolo |
| 7,965,180 B2 | 6/2011 | Koyama |
| 7,967,808 B2 | 6/2011 | Fitzgerald et al. |
| 7,969,473 B2 | 6/2011 | Kotoda |
| 7,972,330 B2 | 7/2011 | Alejandro et al. |
| 7,976,552 B2 | 7/2011 | Suzuki |
| 7,985,239 B2 | 7/2011 | Suzuki |
| 7,988,685 B2 | 8/2011 | Ziaie et al. |
| 8,034,046 B2 | 10/2011 | Eidenschink |
| 8,048,067 B2 | 11/2011 | Davalos et al. |
| 8,057,510 B2 | 11/2011 | Ginn et al. |
| 8,062,306 B2 * | 11/2011 | Nobis et al. .................. 606/113 |
| 8,062,311 B2 | 11/2011 | Litscher et al. |
| 8,066,632 B2 | 11/2011 | Dario et al. |
| 8,075,587 B2 | 12/2011 | Ginn |
| 8,088,062 B2 | 1/2012 | Zwolinski |
| 8,096,459 B2 | 1/2012 | Ortiz et al. |
| 8,118,821 B2 | 2/2012 | Mouw |
| 8,147,424 B2 | 4/2012 | Kassab et al. |
| 8,157,813 B2 | 4/2012 | Ko et al. |
| 8,182,414 B2 | 5/2012 | Handa et al. |
| 2001/0023333 A1 | 9/2001 | Wise et al. |
| 2001/0049497 A1 | 12/2001 | Kalloo et al. |
| 2002/0022771 A1 | 2/2002 | Diokno et al. |
| 2002/0022857 A1 | 2/2002 | Goldsteen et al. |
| 2002/0023353 A1 | 2/2002 | Ting-Kung |
| 2002/0029055 A1 | 3/2002 | Bonutti |
| 2002/0042562 A1 | 4/2002 | Meron et al. |
| 2002/0049439 A1 | 4/2002 | Mulier et al. |
| 2002/0068945 A1 | 6/2002 | Sixto, Jr. et al. |
| 2002/0078967 A1 | 6/2002 | Sixto, Jr. et al. |
| 2002/0082516 A1 | 6/2002 | Stefanchik |
| 2002/0091391 A1 | 7/2002 | Cole et al. |
| 2002/0095164 A1 | 7/2002 | Andreas et al. |
| 2002/0107530 A1 | 8/2002 | Sauer et al. |
| 2002/0133115 A1 | 9/2002 | Gordon et al. |
| 2002/0138086 A1 | 9/2002 | Sixto, Jr. et al. |
| 2002/0147456 A1 | 10/2002 | Diduch et al. |
| 2002/0165592 A1 | 11/2002 | Glukhovsky et al. |
| 2002/0173805 A1 | 11/2002 | Matsuno et al. |
| 2002/0183591 A1 | 12/2002 | Matsuura et al. |
| 2003/0014090 A1 | 1/2003 | Abrahamson |
| 2003/0023255 A1 | 1/2003 | Miles et al. |
| 2003/0036679 A1 | 2/2003 | Kortenbach et al. |
| 2003/0069602 A1 | 4/2003 | Jacobs et al. |
| 2003/0083681 A1 | 5/2003 | Moutafis et al. |
| 2003/0114731 A1 | 6/2003 | Cadeddu et al. |
| 2003/0114732 A1 | 6/2003 | Webler et al. |
| 2003/0120257 A1 | 6/2003 | Houston et al. |
| 2003/0124009 A1 | 7/2003 | Ravi et al. |
| 2003/0130564 A1 | 7/2003 | Martone et al. |
| 2003/0130656 A1 | 7/2003 | Levin |
| 2003/0158521 A1 | 8/2003 | Ameri |
| 2003/0167062 A1 | 9/2003 | Gambale et al. |
| 2003/0171651 A1 | 9/2003 | Page et al. |
| 2003/0176880 A1 | 9/2003 | Long et al. |
| 2003/0191497 A1 | 10/2003 | Cope |
| 2003/0195565 A1 | 10/2003 | Bonutti |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 * | 12/2003 | Okada et al. .................. 600/439 |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0002683 A1 | 1/2004 | Nicholson et al. |
| 2004/0002735 A1 | 1/2004 | Lizardi et al. |
| 2004/0034369 A1 | 2/2004 | Sauer et al. |
| 2004/0054322 A1 | 3/2004 | Vargas |
| 2004/0098007 A1 | 5/2004 | Heiss |
| 2004/0101456 A1 | 5/2004 | Kuroshima et al. |
| 2004/0104999 A1 | 6/2004 | Okada |
| 2004/0116948 A1 | 6/2004 | Sixto, Jr. et al. |
| 2004/0127940 A1 | 7/2004 | Ginn et al. |

| | | | | | |
|---|---|---|---|---|---|
| 2004/0133077 A1 | 7/2004 | Obenchain et al. | 2005/0182429 A1 | 8/2005 | Yamanouchi |
| 2004/0133089 A1 | 7/2004 | Kilcoyne et al. | 2005/0192478 A1 | 9/2005 | Williams et al. |
| 2004/0136779 A1 | 7/2004 | Bhaskar | 2005/0192598 A1 | 9/2005 | Johnson et al. |
| 2004/0138525 A1 | 7/2004 | Saadat et al. | 2005/0192602 A1 | 9/2005 | Manzo |
| 2004/0138529 A1 | 7/2004 | Wiltshire et al. | 2005/0192654 A1 | 9/2005 | Chanduszko et al. |
| 2004/0138587 A1 | 7/2004 | Lyons, IV | 2005/0209624 A1 | 9/2005 | Vijay |
| 2004/0161451 A1 | 8/2004 | Pierce et al. | 2005/0215858 A1 | 9/2005 | Vail, III |
| 2004/0167545 A1 | 8/2004 | Sadler et al. | 2005/0215996 A1 * | 9/2005 | Ouchi ............................ 606/46 |
| 2004/0186350 A1 | 9/2004 | Brenneman et al. | 2005/0216050 A1 | 9/2005 | Sepetka et al. |
| 2004/0193009 A1 | 9/2004 | Jaffe et al. | 2005/0228406 A1 | 10/2005 | Bose |
| 2004/0193146 A1 | 9/2004 | Lee et al. | 2005/0234297 A1 | 10/2005 | Devierre et al. |
| 2004/0193186 A1 | 9/2004 | Kortenbach et al. | 2005/0250983 A1 | 11/2005 | Tremaglio et al. |
| 2004/0193188 A1 | 9/2004 | Francese | 2005/0250990 A1 | 11/2005 | Le et al. |
| 2004/0193189 A1 | 9/2004 | Kortenbach et al. | 2005/0250993 A1 | 11/2005 | Jaeger |
| 2004/0193200 A1 | 9/2004 | Dworschak et al. | 2005/0251166 A1 | 11/2005 | Vaughan et al. |
| 2004/0199052 A1 | 10/2004 | Banik et al. | 2005/0251176 A1 | 11/2005 | Swanstrom et al. |
| 2004/0199159 A1 | 10/2004 | Lee et al. | 2005/0261674 A1 | 11/2005 | Nobis et al. |
| 2004/0206859 A1 | 10/2004 | Chong et al. | 2005/0267492 A1 | 12/2005 | Poncet et al. |
| 2004/0210245 A1 | 10/2004 | Erickson et al. | 2005/0272975 A1 | 12/2005 | McWeeney et al. |
| 2004/0215058 A1 | 10/2004 | Zirps et al. | 2005/0272977 A1 | 12/2005 | Saadat et al. |
| 2004/0225183 A1 | 11/2004 | Michlitsch et al. | 2005/0273084 A1 | 12/2005 | Hinman et al. |
| 2004/0225186 A1 | 11/2004 | Horne, Jr. et al. | 2005/0274935 A1 | 12/2005 | Nelson |
| 2004/0225323 A1 | 11/2004 | Nagase et al. | 2005/0277945 A1 | 12/2005 | Saadat et al. |
| 2004/0230095 A1 | 11/2004 | Stefanchik et al. | 2005/0277951 A1 | 12/2005 | Smith et al. |
| 2004/0230096 A1 | 11/2004 | Stefanchik et al. | 2005/0277952 A1 | 12/2005 | Arp et al. |
| 2004/0230097 A1 | 11/2004 | Stefanchik et al. | 2005/0277954 A1 | 12/2005 | Smith et al. |
| 2004/0230161 A1 | 11/2004 | Zeiner | 2005/0277955 A1 | 12/2005 | Palmer et al. |
| 2004/0243108 A1 | 12/2004 | Suzuki | 2005/0277956 A1 | 12/2005 | Francese et al. |
| 2004/0249246 A1 | 12/2004 | Campos | 2005/0277957 A1 | 12/2005 | Kuhns et al. |
| 2004/0249367 A1 | 12/2004 | Saadat et al. | 2005/0283118 A1 | 12/2005 | Uth et al. |
| 2004/0249394 A1 | 12/2004 | Morris et al. | 2005/0283119 A1 | 12/2005 | Uth et al. |
| 2004/0249443 A1 | 12/2004 | Shanley et al. | 2005/0288555 A1 | 12/2005 | Binmoeller |
| 2004/0254572 A1 | 12/2004 | McIntyre et al. | 2006/0004406 A1 | 1/2006 | Wehrstein et al. |
| 2004/0260198 A1 | 12/2004 | Rothberg et al. | 2006/0004409 A1 | 1/2006 | Nobis et al. |
| 2004/0260337 A1 | 12/2004 | Freed | 2006/0004410 A1 | 1/2006 | Nobis et al. |
| 2005/0004515 A1 | 1/2005 | Hart et al. | 2006/0015009 A1 | 1/2006 | Jaffe et al. |
| 2005/0033265 A1 | 2/2005 | Engel et al. | 2006/0020167 A1 | 1/2006 | Sitzmann |
| 2005/0033277 A1 | 2/2005 | Clague et al. | 2006/0020247 A1 | 1/2006 | Kagan et al. |
| 2005/0033319 A1 | 2/2005 | Gambale et al. | 2006/0025654 A1 | 2/2006 | Suzuki et al. |
| 2005/0033333 A1 | 2/2005 | Smith et al. | 2006/0025781 A1 | 2/2006 | Young et al. |
| 2005/0043690 A1 | 2/2005 | Todd | 2006/0025812 A1 | 2/2006 | Shelton, IV |
| 2005/0049616 A1 | 3/2005 | Rivera et al. | 2006/0025819 A1 | 2/2006 | Nobis et al. |
| 2005/0059963 A1 | 3/2005 | Phan et al. | 2006/0036267 A1 | 2/2006 | Saadat et al. |
| 2005/0065397 A1 | 3/2005 | Saadat et al. | 2006/0041188 A1 | 2/2006 | Dirusso et al. |
| 2005/0065509 A1 | 3/2005 | Coldwell et al. | 2006/0058582 A1 | 3/2006 | Maahs et al. |
| 2005/0065517 A1 | 3/2005 | Chin | 2006/0058776 A1 | 3/2006 | Bilsbury |
| 2005/0070754 A1 | 3/2005 | Nobis et al. | 2006/0064083 A1 | 3/2006 | Khalaj et al. |
| 2005/0070763 A1 | 3/2005 | Nobis et al. | 2006/0069396 A1 | 3/2006 | Meade et al. |
| 2005/0070764 A1 | 3/2005 | Nobis et al. | 2006/0069424 A1 | 3/2006 | Acosta et al. |
| 2005/0080413 A1 | 4/2005 | Canady | 2006/0069425 A1 | 3/2006 | Hillis et al. |
| 2005/0085693 A1 | 4/2005 | Belson et al. | 2006/0069429 A1 | 3/2006 | Spence et al. |
| 2005/0085832 A1 | 4/2005 | Sancoff et al. | 2006/0074413 A1 | 4/2006 | Behzadian |
| 2005/0090837 A1 | 4/2005 | Sixto, Jr. et al. | 2006/0079890 A1 | 4/2006 | Guerra |
| 2005/0090838 A1 | 4/2005 | Sixto, Jr. et al. | 2006/0089528 A1 | 4/2006 | Tartaglia et al. |
| 2005/0096502 A1 | 5/2005 | Khalili | 2006/0095031 A1 | 5/2006 | Ormsby |
| 2005/0101837 A1 | 5/2005 | Kalloo et al. | 2006/0095060 A1 | 5/2006 | Mayenberger et al. |
| 2005/0101838 A1 | 5/2005 | Camillocci et al. | 2006/0100687 A1 | 5/2006 | Fahey et al. |
| 2005/0101984 A1 | 5/2005 | Chanduszko et al. | 2006/0106423 A1 | 5/2006 | Weisel et al. |
| 2005/0107663 A1 | 5/2005 | Saadat et al. | 2006/0111209 A1 | 5/2006 | Hinman et al. |
| 2005/0107664 A1 | 5/2005 | Kalloo et al. | 2006/0111210 A1 | 5/2006 | Hinman et al. |
| 2005/0110881 A1 | 5/2005 | Glukhovsky et al. | 2006/0111704 A1 | 5/2006 | Brenneman et al. |
| 2005/0113847 A1 | 5/2005 | Gadberry et al. | 2006/0129166 A1 | 6/2006 | Lavelle |
| 2005/0119613 A1 | 6/2005 | Moenning et al. | 2006/0135962 A1 | 6/2006 | Kick et al. |
| 2005/0124855 A1 | 6/2005 | Jaffe et al. | 2006/0135971 A1 | 6/2006 | Swanstrom et al. |
| 2005/0125010 A1 | 6/2005 | Smith et al. | 2006/0135984 A1 | 6/2006 | Kramer et al. |
| 2005/0131279 A1 | 6/2005 | Boulais et al. | 2006/0142644 A1 | 6/2006 | Mulac et al. |
| 2005/0131457 A1 | 6/2005 | Douglas et al. | 2006/0142652 A1 | 6/2006 | Keenan |
| 2005/0137454 A1 | 6/2005 | Saadat et al. | 2006/0142790 A1 | 6/2006 | Gertner |
| 2005/0143647 A1 | 6/2005 | Minai et al. | 2006/0142798 A1 | 6/2006 | Holman et al. |
| 2005/0143690 A1 | 6/2005 | High | 2006/0149131 A1 | 7/2006 | Or |
| 2005/0143774 A1 | 6/2005 | Polo | 2006/0149132 A1 | 7/2006 | Iddan |
| 2005/0143803 A1 | 6/2005 | Watson et al. | 2006/0149135 A1 | 7/2006 | Paz |
| 2005/0149087 A1 | 7/2005 | Ahlberg et al. | 2006/0161190 A1 | 7/2006 | Gadberry et al. |
| 2005/0149096 A1 | 7/2005 | Hilal et al. | 2006/0167416 A1 | 7/2006 | Mathis et al. |
| 2005/0159648 A1 | 7/2005 | Freed | 2006/0167482 A1 | 7/2006 | Swain et al. |
| 2005/0165272 A1 | 7/2005 | Okada et al. | 2006/0178560 A1 | 8/2006 | Saadat et al. |
| 2005/0165378 A1 | 7/2005 | Heinrich et al. | 2006/0183975 A1 | 8/2006 | Saadat et al. |
| 2005/0165411 A1 | 7/2005 | Orban, III | 2006/0184161 A1 * | 8/2006 | Maahs et al. ...................... 606/2 |
| 2005/0165429 A1 | 7/2005 | Douglas et al. | 2006/0189844 A1 | 8/2006 | Tien |

| | | | | | |
|---|---|---|---|---|---|
| 2006/0189845 A1 | 8/2006 | Maahs et al. | 2007/0142706 A1 | 6/2007 | Matsui et al. |
| 2006/0190027 A1 | 8/2006 | Downey | 2007/0142710 A1 | 6/2007 | Yokoi et al. |
| 2006/0195084 A1 | 8/2006 | Slater | 2007/0142780 A1 | 6/2007 | Van Lue |
| 2006/0200005 A1 | 9/2006 | Bjork et al. | 2007/0154460 A1 | 7/2007 | Kraft et al. |
| 2006/0200121 A1 | 9/2006 | Mowery | 2007/0156028 A1 | 7/2007 | Van Lue et al. |
| 2006/0200169 A1 | 9/2006 | Sniffin | 2007/0156127 A1 | 7/2007 | Rioux et al. |
| 2006/0200170 A1 | 9/2006 | Aranyi | 2007/0161855 A1 | 7/2007 | Mikkaichi et al. |
| 2006/0200199 A1 | 9/2006 | Bonutti et al. | 2007/0162101 A1 | 7/2007 | Burgermeister et al. |
| 2006/0217665 A1 | 9/2006 | Prosek | 2007/0167901 A1 | 7/2007 | Herrig et al. |
| 2006/0217697 A1 | 9/2006 | Lau et al. | 2007/0173691 A1 | 7/2007 | Yokoi et al. |
| 2006/0217742 A1 | 9/2006 | Messerly et al. | 2007/0173869 A1 | 7/2007 | Gannoe et al. |
| 2006/0217743 A1 | 9/2006 | Messerly et al. | 2007/0173870 A2 | 7/2007 | Zacharias |
| 2006/0229639 A1 | 10/2006 | Whitfield | 2007/0173872 A1 | 7/2007 | Neuenfeldt |
| 2006/0229640 A1 | 10/2006 | Whitfield | 2007/0179525 A1 | 8/2007 | Frecker et al. |
| 2006/0237022 A1 | 10/2006 | Chen et al. | 2007/0179530 A1 | 8/2007 | Tieu et al. |
| 2006/0237023 A1 | 10/2006 | Cox et al. | 2007/0197865 A1 | 8/2007 | Miyake et al. |
| 2006/0241570 A1 | 10/2006 | Wilk | 2007/0198057 A1 | 8/2007 | Gelbart et al. |
| 2006/0247576 A1 | 11/2006 | Poncet | 2007/0203398 A1 | 8/2007 | Bonadio et al. |
| 2006/0247673 A1 | 11/2006 | Voegele et al. | 2007/0203487 A1 | 8/2007 | Sugita |
| 2006/0253004 A1 | 11/2006 | Frisch et al. | 2007/0208336 A1 | 9/2007 | Kim et al. |
| 2006/0253039 A1 | 11/2006 | McKenna et al. | 2007/0208364 A1 | 9/2007 | Smith et al. |
| 2006/0258907 A1 | 11/2006 | Stefanchik et al. | 2007/0213754 A1 | 9/2007 | Mikkaichi et al. |
| 2006/0258908 A1 | 11/2006 | Stefanchik et al. | 2007/0225554 A1 | 9/2007 | Maseda et al. |
| 2006/0258910 A1 | 11/2006 | Stefanchik et al. | 2007/0233040 A1 | 10/2007 | Macnamara et al. |
| 2006/0258954 A1 | 11/2006 | Timberlake et al. | 2007/0244358 A1 | 10/2007 | Lee |
| 2006/0258955 A1 | 11/2006 | Hoffman et al. | 2007/0250038 A1 | 10/2007 | Boulais |
| 2006/0259010 A1 | 11/2006 | Stefanchik et al. | 2007/0250057 A1 | 10/2007 | Nobis et al. |
| 2006/0259073 A1 | 11/2006 | Miyamoto et al. | 2007/0255096 A1 | 11/2007 | Stefanchik et al. |
| 2006/0264752 A1 | 11/2006 | Rubinsky et al. | 2007/0255100 A1 | 11/2007 | Barlow et al. |
| 2006/0264904 A1 | 11/2006 | Kerby et al. | 2007/0255273 A1 | 11/2007 | Fernandez et al. |
| 2006/0264930 A1 | 11/2006 | Nishimura | 2007/0255303 A1 | 11/2007 | Bakos et al. |
| 2006/0270902 A1 | 11/2006 | Igarashi et al. | 2007/0255306 A1 | 11/2007 | Conlon et al. |
| 2006/0271042 A1 | 11/2006 | Latterell et al. | 2007/0260112 A1 | 11/2007 | Rahmani |
| 2006/0271102 A1 | 11/2006 | Bosshard et al. | 2007/0260117 A1 | 11/2007 | Zwolinski et al. |
| 2006/0276835 A1 | 12/2006 | Uchida | 2007/0260121 A1 | 11/2007 | Bakos et al. |
| 2006/0281970 A1 | 12/2006 | Stokes et al. | 2007/0260242 A1 | 11/2007 | Dycus et al. |
| 2006/0282106 A1 | 12/2006 | Cole et al. | 2007/0260273 A1 | 11/2007 | Cropper et al. |
| 2006/0285732 A1 | 12/2006 | Horn et al. | 2007/0270629 A1 | 11/2007 | Charles |
| 2006/0287644 A1 | 12/2006 | Inganas et al. | 2007/0270889 A1 | 11/2007 | Conlon et al. |
| 2006/0287666 A1 | 12/2006 | Saadat et al. | 2007/0270895 A1* | 11/2007 | Nobis et al. .................. 606/170 |
| 2006/0293626 A1 | 12/2006 | Byrum et al. | 2007/0270907 A1 | 11/2007 | Stokes et al. |
| 2007/0002135 A1 | 1/2007 | Glukhovsky | 2007/0282165 A1 | 12/2007 | Hopkins et al. |
| 2007/0005019 A1 | 1/2007 | Okishige | 2007/0282371 A1 | 12/2007 | Lee et al. |
| 2007/0010801 A1 | 1/2007 | Chen et al. | 2007/0293727 A1 | 12/2007 | Goldfarb et al. |
| 2007/0015965 A1 | 1/2007 | Cox et al. | 2007/0299387 A1 | 12/2007 | Williams et al. |
| 2007/0016225 A1 | 1/2007 | Nakao | 2008/0004650 A1 | 1/2008 | George |
| 2007/0032700 A1 | 2/2007 | Fowler et al. | 2008/0015409 A1* | 1/2008 | Barlow et al. ................. 600/106 |
| 2007/0032701 A1 | 2/2007 | Fowler et al. | 2008/0015413 A1 | 1/2008 | Barlow et al. |
| 2007/0043261 A1 | 2/2007 | Watanabe et al. | 2008/0015552 A1 | 1/2008 | Doyle et al. |
| 2007/0043345 A1 | 2/2007 | Davalos et al. | 2008/0021416 A1 | 1/2008 | Arai et al. |
| 2007/0049800 A1 | 3/2007 | Boulais | 2008/0022927 A1 | 1/2008 | Zhang et al. |
| 2007/0049902 A1 | 3/2007 | Griffin et al. | 2008/0027387 A1 | 1/2008 | Grabinsky |
| 2007/0051375 A1 | 3/2007 | Milliman | 2008/0033451 A1 | 2/2008 | Rieber et al. |
| 2007/0060880 A1 | 3/2007 | Gregorich et al. | 2008/0051629 A1 | 2/2008 | Sugiyama et al. |
| 2007/0067017 A1 | 3/2007 | Trapp | 2008/0051735 A1 | 2/2008 | Measamer et al. |
| 2007/0073102 A1 | 3/2007 | Matsuno et al. | 2008/0058586 A1 | 3/2008 | Karpiel |
| 2007/0073269 A1 | 3/2007 | Becker | 2008/0058854 A1 | 3/2008 | Kieturakis et al. |
| 2007/0079924 A1 | 4/2007 | Saadat et al. | 2008/0065169 A1 | 3/2008 | Colliou et al. |
| 2007/0083195 A1 | 4/2007 | Werneth et al. | 2008/0071264 A1 | 3/2008 | Azure |
| 2007/0088370 A1 | 4/2007 | Kahle et al. | 2008/0086172 A1 | 4/2008 | Martin et al. |
| 2007/0100375 A1 | 5/2007 | Mikkaichi et al. | 2008/0097159 A1 | 4/2008 | Ishiguro |
| 2007/0100376 A1 | 5/2007 | Mikkaichi et al. | 2008/0097472 A1 | 4/2008 | Agmon et al. |
| 2007/0106118 A1 | 5/2007 | Moriyama | 2008/0097483 A1 | 4/2008 | Ortiz et al. |
| 2007/0106317 A1 | 5/2007 | Shelton, IV et al. | 2008/0103527 A1 | 5/2008 | Martin et al. |
| 2007/0112251 A1 | 5/2007 | Nakhuda | 2008/0114384 A1 | 5/2008 | Chang et al. |
| 2007/0112331 A1 | 5/2007 | Weber et al. | 2008/0119870 A1 | 5/2008 | Williams |
| 2007/0112342 A1 | 5/2007 | Pearson et al. | 2008/0119891 A1 | 5/2008 | Miles et al. |
| 2007/0112383 A1 | 5/2007 | Conlon et al. | 2008/0125796 A1 | 5/2008 | Graham |
| 2007/0112384 A1 | 5/2007 | Conlon et al. | 2008/0132892 A1 | 6/2008 | Lunsford et al. |
| 2007/0112385 A1 | 5/2007 | Conlon | 2008/0139882 A1 | 6/2008 | Fujimori |
| 2007/0112417 A1 | 5/2007 | Shanley et al. | 2008/0140071 A1 | 6/2008 | Vegesna |
| 2007/0112425 A1 | 5/2007 | Schaller et al. | 2008/0147113 A1 | 6/2008 | Nobis et al. |
| 2007/0118115 A1 | 5/2007 | Artale et al. | 2008/0171907 A1 | 7/2008 | Long et al. |
| 2007/0123840 A1 | 5/2007 | Cox | 2008/0177135 A1 | 7/2008 | Muyari et al. |
| 2007/0129605 A1 | 6/2007 | Schaaf | 2008/0188710 A1 | 8/2008 | Segawa et al. |
| 2007/0129719 A1 | 6/2007 | Kendale et al. | 2008/0188868 A1 | 8/2008 | Weitzner et al. |
| 2007/0129760 A1 | 6/2007 | Demarais et al. | 2008/0200755 A1 | 8/2008 | Bakos |
| 2007/0135709 A1 | 6/2007 | Rioux et al. | 2008/0200762 A1 | 8/2008 | Stokes et al. |
| 2007/0135803 A1 | 6/2007 | Belson | 2008/0200911 A1 | 8/2008 | Long |

| Publication No. | Date | Inventor |
|---|---|---|
| 2008/0200912 A1 | 8/2008 | Long |
| 2008/0200933 A1 | 8/2008 | Bakos et al. |
| 2008/0200934 A1 | 8/2008 | Fox |
| 2008/0208213 A1 | 8/2008 | Benjamin et al. |
| 2008/0221587 A1 | 9/2008 | Schwartz |
| 2008/0221619 A1 | 9/2008 | Spivey et al. |
| 2008/0228213 A1 | 9/2008 | Blakeney et al. |
| 2008/0230972 A1 | 9/2008 | Ganley |
| 2008/0234696 A1 | 9/2008 | Taylor et al. |
| 2008/0243106 A1 | 10/2008 | Coe et al. |
| 2008/0243148 A1 | 10/2008 | Mikkaichi et al. |
| 2008/0243176 A1 | 10/2008 | Weitzner et al. |
| 2008/0249567 A1 | 10/2008 | Kaplan |
| 2008/0262513 A1 | 10/2008 | Stahler et al. |
| 2008/0262540 A1 | 10/2008 | Bangera et al. |
| 2008/0269782 A1 | 10/2008 | Stefanchik et al. |
| 2008/0269783 A1 | 10/2008 | Griffith |
| 2008/0275474 A1 | 11/2008 | Martin et al. |
| 2008/0275475 A1 | 11/2008 | Schwemberger et al. |
| 2008/0287737 A1 | 11/2008 | Dejima |
| 2008/0287983 A1 | 11/2008 | Smith et al. |
| 2008/0300461 A1 | 12/2008 | Shaw et al. |
| 2008/0300547 A1 | 12/2008 | Bakos |
| 2008/0309758 A1 | 12/2008 | Karasawa et al. |
| 2008/0312496 A1 | 12/2008 | Zwolinski |
| 2008/0312499 A1 | 12/2008 | Handa et al. |
| 2008/0312500 A1 | 12/2008 | Asada et al. |
| 2008/0312506 A1 | 12/2008 | Spivey et al. |
| 2008/0319436 A1 | 12/2008 | Daniel et al. |
| 2008/0319439 A1 | 12/2008 | Ootsubu |
| 2009/0005636 A1 | 1/2009 | Pang et al. |
| 2009/0054728 A1 | 2/2009 | Trusty |
| 2009/0062788 A1 | 3/2009 | Long et al. |
| 2009/0062792 A1 | 3/2009 | Vakharia et al. |
| 2009/0062795 A1 | 3/2009 | Vakharia et al. |
| 2009/0069634 A1 | 3/2009 | Larkin |
| 2009/0076499 A1 | 3/2009 | Azure |
| 2009/0078736 A1 | 3/2009 | Van Lue |
| 2009/0082776 A1 | 3/2009 | Cresina |
| 2009/0082779 A1 | 3/2009 | Nakao |
| 2009/0112059 A1 | 4/2009 | Nobis |
| 2009/0112062 A1 | 4/2009 | Bakos |
| 2009/0112063 A1 | 4/2009 | Bakos et al. |
| 2009/0125042 A1 | 5/2009 | Mouw |
| 2009/0131751 A1 | 5/2009 | Spivey et al. |
| 2009/0131932 A1 | 5/2009 | Vakharia et al. |
| 2009/0131933 A1 | 5/2009 | Ghabrial et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0143818 A1 | 6/2009 | Faller et al. |
| 2009/0149710 A1 | 6/2009 | Stefanchik et al. |
| 2009/0177031 A1 | 7/2009 | Surti et al. |
| 2009/0177219 A1 | 7/2009 | Conlon |
| 2009/0182332 A1 | 7/2009 | Long et al. |
| 2009/0192344 A1 | 7/2009 | Bakos et al. |
| 2009/0192534 A1 | 7/2009 | Ortiz et al. |
| 2009/0198231 A1 | 8/2009 | Esser et al. |
| 2009/0198253 A1 | 8/2009 | Omori |
| 2009/0216248 A1 | 8/2009 | Uenohara et al. |
| 2009/0227828 A1 | 9/2009 | Swain et al. |
| 2009/0248055 A1 | 10/2009 | Spivey et al. |
| 2009/0269317 A1 | 10/2009 | Davalos |
| 2009/0281559 A1 | 11/2009 | Swain et al. |
| 2009/0287206 A1 | 11/2009 | Jun |
| 2009/0287236 A1 | 11/2009 | Bakos et al. |
| 2009/0292164 A1 | 11/2009 | Yamatani |
| 2009/0299135 A1 | 12/2009 | Spivey |
| 2009/0299143 A1 | 12/2009 | Conlon et al. |
| 2009/0299362 A1 | 12/2009 | Long et al. |
| 2009/0299385 A1 | 12/2009 | Stefanchik et al. |
| 2009/0299406 A1 | 12/2009 | Swain et al. |
| 2009/0299409 A1 | 12/2009 | Coe et al. |
| 2009/0306683 A1 | 12/2009 | Zwolinski et al. |
| 2009/0322864 A1 | 12/2009 | Karasawa et al. |
| 2009/0326332 A1 | 12/2009 | Carter |
| 2009/0326561 A1 | 12/2009 | Carroll, II et al. |
| 2010/0010294 A1 | 1/2010 | Conlon et al. |
| 2010/0010298 A1 | 1/2010 | Bakos et al. |
| 2010/0010299 A1 | 1/2010 | Bakos et al. |
| 2010/0010303 A1 | 1/2010 | Bakos |
| 2010/0010510 A1 | 1/2010 | Stefanchik |
| 2010/0010511 A1 | 1/2010 | Harris et al. |
| 2010/0023032 A1 | 1/2010 | Granja Filho |
| 2010/0030211 A1 | 2/2010 | Davalos et al. |
| 2010/0036198 A1 | 2/2010 | Tacchino et al. |
| 2010/0042045 A1 | 2/2010 | Spivey |
| 2010/0048990 A1 | 2/2010 | Bakos |
| 2010/0049190 A1 | 2/2010 | Long et al. |
| 2010/0049223 A1 | 2/2010 | Granja Filho |
| 2010/0056861 A1 | 3/2010 | Spivey |
| 2010/0056862 A1 | 3/2010 | Bakos |
| 2010/0056864 A1 | 3/2010 | Lee |
| 2010/0057085 A1 | 3/2010 | Holcomb et al. |
| 2010/0057108 A1 | 3/2010 | Spivey et al. |
| 2010/0063538 A1 | 3/2010 | Spivey et al. |
| 2010/0076451 A1 | 3/2010 | Zwolinski et al. |
| 2010/0081877 A1 | 4/2010 | Vakharia |
| 2010/0087813 A1 | 4/2010 | Long |
| 2010/0091128 A1 | 4/2010 | Ogasawara et al. |
| 2010/0113872 A1 | 5/2010 | Asada et al. |
| 2010/0121362 A1 | 5/2010 | Clague et al. |
| 2010/0130817 A1 | 5/2010 | Conlon |
| 2010/0130975 A1 | 5/2010 | Long |
| 2010/0131005 A1* | 5/2010 | Conlon .................... 606/207 |
| 2010/0152539 A1 | 6/2010 | Ghabrial et al. |
| 2010/0152609 A1 | 6/2010 | Zwolinski et al. |
| 2010/0152746 A1 | 6/2010 | Ceniccola et al. |
| 2010/0179510 A1 | 7/2010 | Fox et al. |
| 2010/0179530 A1 | 7/2010 | Long et al. |
| 2010/0191050 A1 | 7/2010 | Zwolinski |
| 2010/0191267 A1 | 7/2010 | Fox |
| 2010/0198005 A1 | 8/2010 | Fox |
| 2010/0198149 A1 | 8/2010 | Fox |
| 2010/0198244 A1 | 8/2010 | Spivey et al. |
| 2010/0198248 A1 | 8/2010 | Vakharia |
| 2010/0217367 A1 | 8/2010 | Belson |
| 2010/0249700 A1 | 9/2010 | Spivey |
| 2010/0261994 A1 | 10/2010 | Davalos et al. |
| 2010/0286791 A1 | 11/2010 | Goldsmith |
| 2010/0298642 A1 | 11/2010 | Trusty et al. |
| 2010/0312056 A1 | 12/2010 | Galperin et al. |
| 2010/0331622 A2 | 12/2010 | Conlon |
| 2010/0331758 A1 | 12/2010 | Davalos et al. |
| 2010/0331774 A2 | 12/2010 | Spivey |
| 2011/0077476 A1 | 3/2011 | Rofougaran |
| 2011/0093009 A1 | 4/2011 | Fox |
| 2011/0098694 A1 | 4/2011 | Long |
| 2011/0098704 A1 | 4/2011 | Long et al. |
| 2011/0105850 A1 | 5/2011 | Voegele et al. |
| 2011/0106221 A1 | 5/2011 | Neal, II et al. |
| 2011/0112434 A1 | 5/2011 | Ghabrial et al. |
| 2011/0115891 A1 | 5/2011 | Trusty |
| 2011/0124964 A1 | 5/2011 | Nobis |
| 2011/0152609 A1 | 6/2011 | Trusty et al. |
| 2011/0152610 A1 | 6/2011 | Trusty et al. |
| 2011/0152612 A1 | 6/2011 | Trusty et al. |
| 2011/0152858 A1 | 6/2011 | Long et al. |
| 2011/0152859 A1 | 6/2011 | Long et al. |
| 2011/0152878 A1 | 6/2011 | Trusty et al. |
| 2011/0152923 A1 | 6/2011 | Fox |
| 2011/0160514 A1 | 6/2011 | Long et al. |
| 2011/0190659 A1 | 8/2011 | Long et al. |
| 2011/0190764 A1 | 8/2011 | Long et al. |
| 2011/0193948 A1 | 8/2011 | Amling et al. |
| 2011/0245619 A1 | 10/2011 | Holcomb |
| 2011/0285488 A1 | 11/2011 | Scott et al. |
| 2011/0306971 A1 | 12/2011 | Long |
| 2012/0004502 A1 | 1/2012 | Weitzner et al. |
| 2012/0088965 A1 | 4/2012 | Stokes et al. |
| 2012/0089089 A1 | 4/2012 | Swain et al. |
| 2012/0089093 A1 | 4/2012 | Trusty |
| 2012/0116155 A1 | 5/2012 | Trusty |
| 2012/0179148 A1 | 7/2012 | Conlon |
| 2012/0191075 A1 | 7/2012 | Trusty |
| 2012/0191076 A1 | 7/2012 | Voegele et al. |
| 2012/0220998 A1 | 8/2012 | Long et al. |

| | | | |
|---|---|---|---|
| 2012/0220999 | A1 | 8/2012 | Long |
| 2012/0221002 | A1 | 8/2012 | Long et al. |
| 2012/0238796 | A1 | 9/2012 | Conlon |

FOREIGN PATENT DOCUMENTS

| | | | |
|---|---|---|---|
| DE | 4323585 A1 | 1/1995 | |
| DE | 19713797 A1 | 10/1997 | |
| DE | 19757056 B4 | 8/2008 | |
| DE | 102006027873 B4 | 10/2009 | |
| EP | 0086338 A1 | 8/1983 | |
| EP | 0286415 A2 | 10/1988 | |
| EP | 0589454 A2 | 3/1994 | |
| EP | 0464479 B1 | 3/1995 | |
| EP | 0529675 B1 | 2/1996 | |
| EP | 0621009 B1 | 7/1997 | |
| EP | 0724863 B1 | 7/1999 | |
| EP | 0760629 B1 | 11/1999 | |
| EP | 0818974 B1 | 7/2001 | |
| EP | 1281356 A2 | 2/2003 | |
| EP | 0947166 B1 | 5/2003 | |
| EP | 0836832 B1 | 12/2003 | |
| EP | 1402837 A1 | 3/2004 | |
| EP | 0744918 B1 | 4/2004 | |
| EP | 0931515 B1 | 8/2004 | |
| EP | 0941128 B1 | 10/2004 | |
| EP | 1411843 B1 | 10/2004 | |
| EP | 1150614 B1 | 11/2004 | |
| EP | 1477104 A1 | 11/2004 | |
| EP | 1481642 A1 | 12/2004 | |
| EP | 1493391 A1 | 1/2005 | |
| EP | 0848598 B1 | 2/2005 | |
| EP | 1281360 B1 | 3/2005 | |
| EP | 1568330 A1 | 8/2005 | |
| EP | 1452143 B1 | 9/2005 | |
| EP | 1616527 A2 | 1/2006 | |
| EP | 1006888 B1 | 3/2006 | |
| EP | 1629764 A1 | 3/2006 | |
| EP | 1013229 B1 | 6/2006 | |
| EP | 1721561 A1 | 11/2006 | |
| EP | 1153578 B1 | 3/2007 | |
| EP | 1334696 B1 | 3/2007 | |
| EP | 1769766 A1 | 4/2007 | |
| EP | 1836971 A2 | 9/2007 | |
| EP | 1836980 A1 | 9/2007 | |
| EP | 1854421 A2 | 11/2007 | |
| EP | 1857061 A1 | 11/2007 | |
| EP | 1875876 A1 | 1/2008 | |
| EP | 1891881 A1 | 2/2008 | |
| EP | 1902663 A1 | 3/2008 | |
| EP | 1477106 B1 | 6/2008 | |
| EP | 1949844 A1 | 7/2008 | |
| EP | 1518499 B1 | 8/2008 | |
| EP | 1582138 B1 | 9/2008 | |
| EP | 1709918 B1 | 10/2008 | |
| EP | 1985226 A2 | 10/2008 | |
| EP | 1994904 A1 | 11/2008 | |
| EP | 1707130 B1 | 12/2008 | |
| EP | 0723462 B1 | 3/2009 | |
| EP | 1769749 B1 | 11/2009 | |
| EP | 1493397 B1 | 9/2011 | |
| FR | 2731610 A1 | 9/1996 | |
| GB | 330629 A | 6/1930 | |
| GB | 2335860 A | 10/1999 | |
| GB | 2403909 A | 1/2005 | |
| GB | 2421190 A | 6/2006 | |
| GB | 2443261 A | 4/2008 | |
| JP | 56-46674 | 4/1981 | |
| JP | 63309252 A | 12/1988 | |
| JP | 4038960 A | 2/1992 | |
| JP | 8-29699 A | 2/1996 | |
| JP | 2000245683 A | 9/2000 | |
| JP | 2002-369791 A | 12/2002 | |
| JP | 2003-088494 A | 3/2003 | |
| JP | 2003-235852 A | 8/2003 | |
| JP | 2004-33525 A | 2/2004 | |
| JP | 2004-065745 A | 3/2004 | |
| JP | 2005-121947 A | 5/2005 | |
| JP | 2005-261514 A | 9/2005 | |
| JP | 2006297005 A | 11/2006 | |
| NL | 1021295 C2 | 2/2004 | |
| SU | 194230 | 5/1967 | |
| SU | 980703 | 12/1982 | |
| WO | WO 84/01707 A1 | 5/1984 | |
| WO | WO 93/10850 A1 | 6/1993 | |
| WO | WO 95/09666 A1 | 4/1995 | |
| WO | WO 98/01080 A1 | 1/1998 | |
| WO | WO 99/00060 A1 | 1/1999 | |
| WO | WO 00/35358 A1 | 6/2000 | |
| WO | WO 01/10319 A1 | 2/2001 | |
| WO | WO 01/26708 A1 | 4/2001 | |
| WO | WO 01/41627 A2 | 6/2001 | |
| WO | WO 01/58360 A2 | 8/2001 | |
| WO | WO 02/11621 A2 | 2/2002 | |
| WO | WO 02/34122 A2 | 5/2002 | |
| WO | WO 02/094082 A2 | 11/2002 | |
| WO | WO 03/047684 A2 | 6/2003 | |
| WO | WO 03/059412 A2 | 7/2003 | |
| WO | WO 03/081761 A2 | 10/2003 | |
| WO | WO 03/082129 A2 | 10/2003 | |
| WO | WO 2004/006789 A1 | 1/2004 | |
| WO | WO 2004/028613 A2 | 4/2004 | |
| WO | WO 2004/037123 A1 | 5/2004 | |
| WO | WO 2004/037149 A1 | 5/2004 | |
| WO | WO 2004/052221 A1 | 6/2004 | |
| WO | WO 2004/086984 A1 | 10/2004 | |
| WO | WO 2005/009211 A2 | 2/2005 | |
| WO | WO 2005/018467 A2 | 3/2005 | |
| WO | WO 2005/037088 A2 | 4/2005 | |
| WO | WO 2005/048827 A1 | 6/2005 | |
| WO | WO 2005/065284 A2 | 7/2005 | |
| WO | WO 2005/097019 A2 | 10/2005 | |
| WO | WO 2005/097234 A2 | 10/2005 | |
| WO | WO 2005/112810 A2 | 12/2005 | |
| WO | WO 2005/120363 A1 | 12/2005 | |
| WO | WO 2005/122866 A1 | 12/2005 | |
| WO | WO 2006/007399 A1 | 1/2006 | |
| WO | WO 2006/012630 A2 | 2/2006 | |
| WO | WO 2006/040109 A1 | 4/2006 | |
| WO | WO 2006/041881 A2 | 4/2006 | |
| WO | WO 2006/060405 A2 | 6/2006 | |
| WO | WO 2006/110733 A2 | 10/2006 | |
| WO | WO 2006/113216 A2 | 10/2006 | |
| WO | WO 2007/013059 A2 | 2/2007 | |
| WO | WO 2007/014063 A2 | 2/2007 | |
| WO | WO 2007/048085 A2 | 4/2007 | |
| WO | WO 2007/063550 A2 | 6/2007 | |
| WO | WO 2007/100067 A1 | 9/2007 | |
| WO | WO 2007/109171 A2 | 9/2007 | |
| WO | WO 2008/005433 A1 | 1/2008 | |
| WO | WO 2008/033356 A2 | 3/2008 | |
| WO | WO 2008/041225 A2 | 4/2008 | |
| WO | WO 2008/076337 A1 | 6/2008 | |
| WO | WO 2008/076800 A2 | 6/2008 | |
| WO | WO 2008/079440 A2 | 7/2008 | |
| WO | WO 2008/101075 A2 | 8/2008 | |
| WO | WO 2008/102154 A2 | 8/2008 | |
| WO | WO 2008/108863 A2 | 9/2008 | |
| WO | WO 2008/151237 A1 | 12/2008 | |
| WO | WO 2009/021030 A1 | 2/2009 | |
| WO | WO 2009/027065 A1 | 3/2009 | |
| WO | WO 2009/029065 A1 | 3/2009 | |
| WO | WO 2009/032623 A2 | 3/2009 | |
| WO | WO 2009/121017 A1 | 10/2009 | |
| WO | WO 2010/027688 A1 | 3/2010 | |
| WO | WO 2010/056716 A2 | 5/2010 | |
| WO | WO 2010/080974 A2 | 7/2010 | |
| WO | WO 2010/088481 A1 | 8/2010 | |

OTHER PUBLICATIONS

Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.

Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.

Ogando, "Prototype Tools That Go With the Flow," Design News, 2 pages, Jul. 17, 2006.

Edd, et al., "In Vivo Results of a New Focal Tissue Ablation Technique: Irreversible Electroporation," IEEE Trans Biomed Eng, vol. 53, pp. 1409-1415, 2006.
Kennedy, et al., "High-Burst-Strength, Feedback-Controlled Bipolar Vessel Sealing," Surgical Endoscopy, vol. 12, pp. 876-878 (1998).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).
K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).
K. Sumiyama et al., "Submucosal Endoscopy with Mucosal Flap Safety Valve," Gastrointest Endosc. Apr. 2007, vol. 65(4) pp. 694-695 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
K. Sumiyama et al., "Endoscopic Caps," Tech. Gastrointest. Endosc., vol. 8, pp. 28-32, 2006.
"Z-Offset Technique Used in the Introduction of Trocar During Laparoscopic Surgery," M.S. Hershey NOTES Presentation to EES NOTES Development Team, Sep. 27, 2007.
F.N. Denans, Nouveau Procede Pour La Guerison Des Plaies Des Intestines. Extrait Des Seances De La Societe Royale De Medecine De Marseille, Pendant Le Mois De Decembre 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).
I. Fraser, "An Historical Perspective on Mechanical Aids in Intestinal Anastamosis," Surg. Gynecol. Obstet. (Oct. 1982), vol. 155, pp. 566-574.
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.
C. Cope, "Creation of Compression Gastroenterostomy by Means of the Oral, Percutaneous, or Surgical Introduction of Magnets: Feasibility Study in Swine," J. Vasc Interv Radiol, (1995), vol. 6(4), pp. 539-545.
J.W. Hazey et al., "Natural Orifice Transgastric Endoscopic Peritoneoscopy in Humans: Initial Clinical Trial," Surg Endosc, (Jan. 2008), vol. 22(1), pp. 16-20.
N. Chopita et al., "Endoscopic Gastroenteric Anastamosis Using Magnets," Endoscopy, (2005), vol. 37(4), pp. 313-317.
C. Cope et al., "Long Term Patency of Experimental Magnetic Compression Gastroenteric Anastamoses Achieved with Covered Stents," Gastrointest Endosc, (2001), vol. 53, pp. 780-784.
H. Okajima et al., "Magnet Compression Anastamosis for Bile Duct Stenosis After Duct to Duct Biliary Reconstruction in Living Donor Liver Transplantation," Liver Transplantation (2005), pp. 473-475.
A. Fritscher-Ravens et al., "Transluminal Endosurgery: Single Lumen Access Anastamotic Device for Flexible Endoscopy," Gastrointestinal Endosc, (2003), vol. 58(4), pp. 585-591.
G.A. Hallenbeck, M.D. et al., "An Instrument for Colorectal Anastomosis Without Sutruves," Dis col. Rectum, (1963), vol. 5, pp. 98-101.
T. Hardy, Jr., M.D. et al., "A Biofragmentable Ring for Sutureless Bowel Anastomosis. An Experimental Study," Dis Col Rectum, (1985), vol. 28, pp. 484-490.
P. O'Neill, M.D. et al., "Nonsuture Intestinal Anastomosis," Am J. Surg, (1962), vol. 104, pp. 761-767.
C.P. Swain, M.D. et al., "Anastomosis at Flexible Endoscopy: An Experimental Study of Compression Button Gastrojejunostomy," Gastrointest Endosc, (1991), vol. 37, pp. 628-632.
J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.
USGI® EndoSurgical Operating System—g-Prox® Tissue Grasper/Approximation Device; [online] URL: http://www.usgimedical.com/eos/components-gprox.htm—accessed May 30, 2008 (2 pages).

Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.
Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).
ERCP; Jackson Siegelbaum Gastroenterology; [online] URL: http://www.gicare.com/pated/epdgs20.htm; accessed Feb. 21, 2008 (3 pages).
D.G. Fong et al., "Transcolonic Ventral Wall Hernia Mesh Fixation in a Porcine Model," Endoscopy 2007; 39: 865-869.
B. Rubinsky, Ph.D., "Irreversible Electroporation in Medicine," Technology in Cancer Research and Treatment, vol. 6, No. 4, Aug. 2007, pp. 255-259.
D.B. Nelson, MD et al., "Endoscopic Hemostatic Devices," Gastrointestinal Endoscopy, vol. 54, No. 6, 2001, pp. 833-840.
CRE™ Pulmonary Balloon Dilator; [online] URL: http://www.bostonscientific.com/Device.bsci?page=HCP_Overview&navRelId=1000.1003&method=D..., accessed Jul. 18, 2008 (4 pages).
U.S. Appl. No. 11/744,271, filed May 4, 2007.
U.S. Appl. No. 11/744,279, filed May 4, 2007.
U.S. Appl. No. 11/796,035, filed Apr. 26, 2007.
U.S. Appl. No. 11/796,357, filed Apr. 27, 2007.
U.S. Appl. No. 11/894,358, filed Aug. 21, 2007.
U.S. Appl. No. 11/897,676, filed Aug. 31, 2007.
U.S. Appl. No. 11/968,810, filed Jan. 3, 2008.
U.S. Appl. No. 11/981,070, filed Oct. 31, 2007.
U.S. Appl. No. 11/981,078, filed Oct. 31, 2007.
U.S. Appl. No. 11/981,134, filed Oct. 31, 2007.
U.S. Appl. No. 11/986,084, filed Nov. 20, 2007.
U.S. Appl. No. 11/986,420, filed Nov. 21, 2007.
U.S. Appl. No. 11/986,489, filed Nov. 21, 2007.
U.S. Appl. No. 11/998,370, filed Nov. 29, 2007.
U.S. Appl. No. 12/014,417, filed Jan. 5, 2008.
U.S. Appl. No. 12/019,461, filed Jan. 24, 2008.
U.S. Appl. No. 12/045,318, filed Mar. 10, 2008.
U.S. Appl. No. 12/109,673, filed Apr. 25, 2008.
U.S. Appl. No. 12/109,699, filed Apr. 25, 2008.
U.S. Appl. No. 12/115,916, filed May 6, 2008.
U.S. Appl. No. 12/122,031, filed May 16, 2008.
U.S. Appl. No. 12/129,784, filed May 30, 2008.
U.S. Appl. No. 12/129,880, filed May 30, 2008.
U.S. Appl. No. 12/202,740, filed Sep. 2, 2008.
U.S. Appl. No. 12/130,023, filed May 30, 2008.
U.S. Appl. No. 12/130,224, filed May 30, 2008.
U.S. Appl. No. 12/130,652, filed May 30, 2008.
U.S. Appl. No. 12/133,109, filed Jun. 4, 2008.
U.S. Appl. No. 12/130,010, filed May 30, 2008.
U.S. Appl. No. 12/163,255, filed Jun. 27, 2008.
U.S. Appl. No. 12/169,868, filed Jul. 9, 2008.
U.S. Appl. No. 12/170,862, filed Jul. 10, 2008.
U.S. Appl. No. 12/172,752, filed Jul. 14, 2008.
U.S. Appl. No. 12/172,766, filed Jul. 14, 2008.
U.S. Appl. No. 12/172,782, filed Jul. 14, 2008.
U.S. Appl. No. 11/762,855, filed Jun. 14, 2007.
U.S. Appl. No. 12/192,372, filed Aug. 15, 2008.
U.S. Appl. No. 12/203,330, filed Sep. 3, 2008.
U.S. Appl. No. 12/197,749, filed Aug. 25, 2008.
U.S. Appl. No. 12/197,653, filed Aug. 25, 2008.
U.S. Appl. No. 12/203,458, filed Sep. 3, 2008.
U.S. Appl. No. 12/201,812, filed Aug. 29, 2008.
U.S. Appl. No. 12/207,306, filed Sep. 9, 2008.
U.S. Appl. No. 12/243,334, filed Oct. 1, 2008.
U.S. Appl. No. 12/234,425, filed Sep. 19, 2008.
U.S. Appl. No. 11/756,914, filed Jun. 1, 2007.
U.S. Appl. No. 12/060,601, filed Apr. 1, 2008.
International Search Report for PCT/US2009/046210, Jul. 24, 2009 (8 pages).

J.D. Paulson, M.D., et al., "Development of Flexible Culdoscopy," The Journal of the American Association of Gynecologic Laparoscopists, Nov. 1999, vol. 6, No. 4, pp. 487-490.

H. Seifert, et al., "Retroperitoneal Endoscopic Debridement for Infected Peripancreatic Necrosis," The Lancet, Research Letters, vol. 356, Aug. 19, 2000, pp. 653-655.

K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Accepted Mar. 31, 1998).

D. Wilhelm et al., "An Innovative, Safe and Sterile Sigmoid Access (ISSA) for NOTES," Endoscopy 2007, vol. 39, pp. 401-406.

Nakazawa et al., "Radiofrequency Ablation of Hepatocellular Carcinoma: Correlation Between Local Tumor Progression After Ablation and Ablative Margin," AJR, 188, pp. 480-488 (Feb. 2007).

Miklavčič et al., "A validated model of in vivo electric field distribution in tissues for electrochemotherapy and for DNA electrotransfer for gene therapy," Biochimica et Biophysica Acta, 1523, pp. 73-83 (2000).

Evans, "Ablative and cathether-delivered therapies for colorectal liver metastases (CRLM)," EJSO, 33, pp. S64-S75 (2007).

Wong et al., "Combined Percutaneous Radiofrequency Ablation and Ethanol Injection for Hepatocellular Carcinoma in High-Risk Locations," AJR, 190, pp. W187-W195 (2008).

Heller et al., "Electrically mediated plasmid DNA delivery to hepatocellular carcinomas in vivo," Gene Therapy, 7, pp. 826-829 (2000).

Widera et al., "Increased DNA Vaccine Delivery and Immunogenicity by Electroporation In Vivo," The Journal of Immunology, 164, pp. 4635-4640 (2000).

Weaver et al., "Theory of electroporation: A review," Bioelectrochemistry and Bioenergetics, 41, pp. 135-160 (1996).

Mulier et al., "Radiofrequency Ablation Versus Resection for Resectable Colorectal Liver Metastases: Time for a Randomized Trial?" Annals of Surgical Oncology, 15(1), pp. 144-157 (2008).

Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).

Guyton et al., "Membrane Potentials and Action Potentials," W.B. Sanders, ed. Textbook of Medical Physiology, p. 56 (2000).

Guyton et al., "Contraction of Skeletal Muscle," Textbook of Medical Physiology, pp. 82-84 (2000).

"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).

"Ethicon Endo-Surgery Studies Presented at DDW Demonstrate Potential of Pure NOTES Surgery With Company's Toolbox," Jun. 3, 2009 Press Release; URL http://www.jnj.com/connect/news/product/20090603_120000; accessed Aug. 28, 2009 (3 pages).

Castellvi et al., "Hybrid Transvaginal NOTES Sleeve Gastrectomy in a Porcine Model Using a Magnetically Anchored Camera and Novel Instrumentation," Abstract submitted along with Poster at SAGES Annual Meeting in Phoenix, AZ, Apr. 22, 2009 (1 page).

Castellvi et al., "Hybrid Transvaginal NOTES Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).

U.S. Appl. No. 12/277,975, filed Nov. 25, 2008.
U.S. Appl. No. 12/277,957, filed Nov. 25, 2008.
U.S. Appl. No. 12/332,938, filed Dec. 11, 2008.
U.S. Appl. No. 12/337,340, filed Dec. 17, 2008.
U.S. Appl. No. 12/352,451, filed Jan. 12, 2009.
U.S. Appl. No. 12/359,824, filed Jan. 26, 2009.
U.S. Appl. No. 12/352,375, filed Jan. 12, 2009.
U.S. Appl. No. 12/359,053, filed Jan. 23, 2009.
U.S. Appl. No. 12/362,826, filed Jan. 30, 2009.
U.S. Appl. No. 12/363,137, filed Jan. 30, 2009.
U.S. Appl. No. 12/364,172, filed Feb. 2, 2009.
U.S. Appl. No. 12/364,256, filed Feb. 2, 2009.
U.S. Appl. No. 12/413,479, filed Mar. 27, 2009.
U.S. Appl. No. 12/468,462, filed May 19, 2009.
U.S. Appl. No. 12/607,252, filed Oct. 28, 2009.
U.S. Appl. No. 12/580,400, filed Oct. 16, 2009.
U.S. Appl. No. 12/607,388, filed Oct. 28, 2009.
U.S. Appl. No. 12/612,911, filed Nov. 5, 2009.
U.S. Appl. No. 12/614,143, filed Nov. 6, 2009.
U.S. Appl. No. 12/617,998, filed Nov. 13, 2009.

Written Opinion for PCT/US2009/046210, Jul. 24, 2009 (8 pages).
International Preliminary Report on Patentability for PCT/US2009/046210, Jul. 24, 2009 (8 pages).
Ethicon, Inc., "Wound Closure Manual: Chapter 3 (The Surgical Needle)," 15 pages, (1994).
OCTO Port Modular Laparoscopy System for Single Incision Access, Jan. 4, 2010; URL http://www.medgadget.com/archives/2010/01/octo_port_modular_laparo...; accessed Jan. 5, 2010 (4 pages).
Hakko Retractors, obtained Aug. 25, 2009 (5 pages).
Zadno et al., "Linear Superelasticity in Cold-Worked Ni—Ti," Engineering Aspects of Shape Memory Alloys, pp. 414-419 (1990).

U.S. Appl. No. 12/752,701, filed Apr. 1, 2010.
U.S. Appl. No. 13/013,131, filed Jan. 25, 2011.
U.S. Appl. No. 13/013,147, filed Jan. 25, 2011.
U.S. Appl. No. 12/900,132, filed Oct. 7, 2010.
U.S. Appl. No. 12/939,441, filed Nov. 4, 2010.
U.S. Appl. No. 12/902,531, filed Oct. 12, 2010.
U.S. Appl. No. 12/902,550, filed Oct. 12, 2010.

Jolly et al., Properties and Applications of Commercial Magnetorheological Fluids. SPIE 5th Annual Int. Symposium on Smart Structures and Materials, 1998 (18 pages).

U.S. Appl. No. 13/036,895, filed Feb. 28, 2011.
U.S. Appl. No. 13/036,908, filed Feb. 28, 2011.
U.S. Appl. No. 13/267,251, filed Oct. 6, 2011.
U.S. Appl. No. 13/325,791, filed Dec. 14, 2011.
U.S. Appl. No. 13/352,495, filed Jan. 18, 2012.
U.S. Appl. No. 13/399,358, filed Feb. 17, 2012.
U.S. Appl. No. 13/420,805, filed Mar. 15, 2012.
U.S. Appl. No. 13/420,818, filed Mar. 15, 2012.
U.S. Appl. No. 13/425,103, filed Mar. 20, 2012.

* cited by examiner

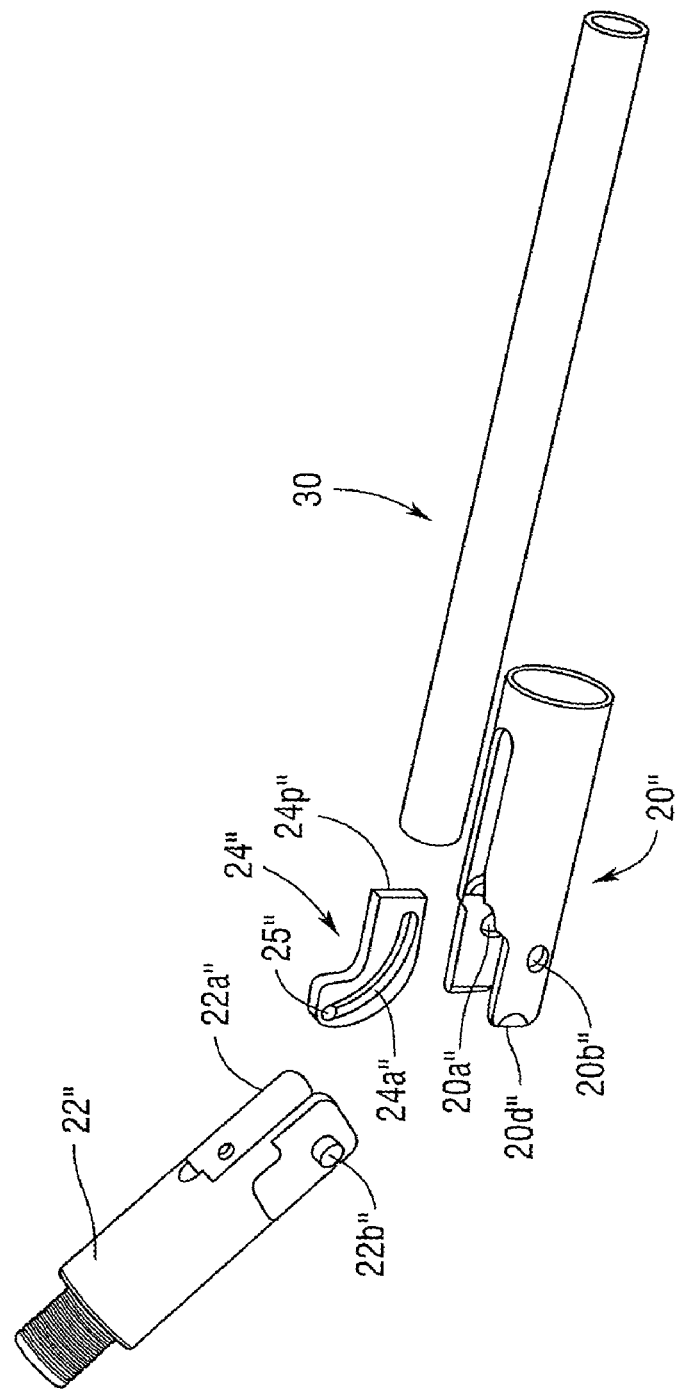

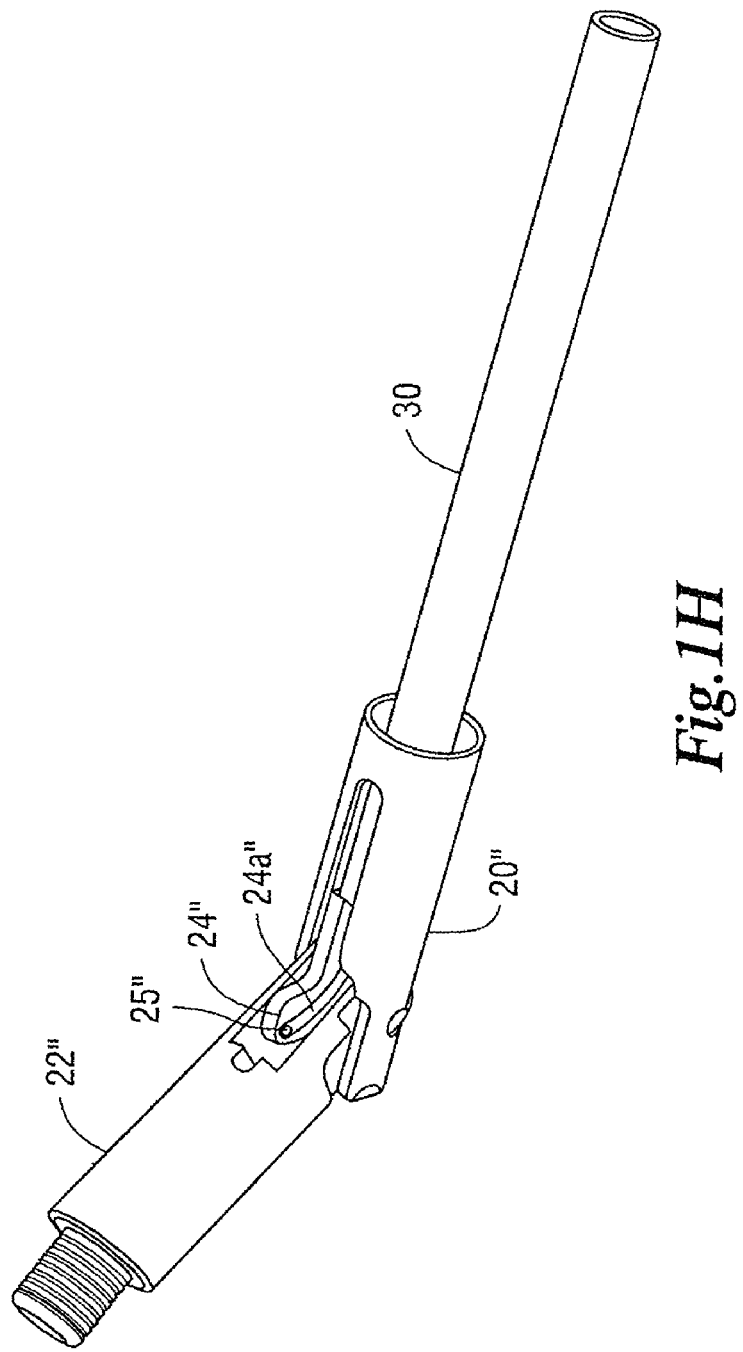

MANUALLY ARTICULATING DEVICES

BACKGROUND

In laparoscopic surgical procedures, a small incision is made in the body and an elongate shaft of a surgical device is inserted through the incision to position a distal end of the shaft at a surgical site. In endoscopic procedures, the elongate shaft of a surgical device is inserted through a natural orifice, such as the mouth or anus, and is advanced along a pathway to position a distal end of the device at a surgical site. Endoscopic procedures typically require the use of a flexible shaft to accommodate the tortuous pathway of the body lumen, whereas rigid shafts can be used in laparoscopic procedures. These tools can be used to engage and/or treat tissue in a number of ways to achieve a diagnostic or therapeutic effect.

Many current laparoscopic and endoscopic devices utilize articulating effectors to provide the user with more control over the orientation of the working end of the instrument. Integration of the controls for articulating, as well as actuating, a working end of a laparoscopic or endoscopic device tend to be complicated by the size constraints of the relatively small pathway through which it is inserted. The controls for an endoscopic device are further complicated by the flexibility of the shaft. Generally, the control motions are all transferred through the shaft as longitudinal translations, which can interfere with the flexibility of the shaft. There is also a desire to lower the force necessary to articulate and/or actuate the working end to a level that all or a great majority of surgeons can handle. One known solution to lower the force-to-fire is to use electrical motors. However, surgeons typically prefer to experience feedback from the working end to assure proper operation of the end effector. The user-feedback effects are not suitably realizable in present motor-driven devices. What is needed is an improvement over the foregoing.

FIGURES

The novel features of the various embodiments are set forth with particularity in the appended claims. The various embodiments, however, both as to organization and methods of operation, together with further advantages thereof, may best be understood by reference to the following description, taken in conjunction with the accompanying drawings as follows:

FIG. 1G is a perspective view of a three-bar linkage according to one embodiment;

FIG. 1H is an assembled view of the three-bar linkage of FIG. 1G;

DESCRIPTION

Figure 1A:
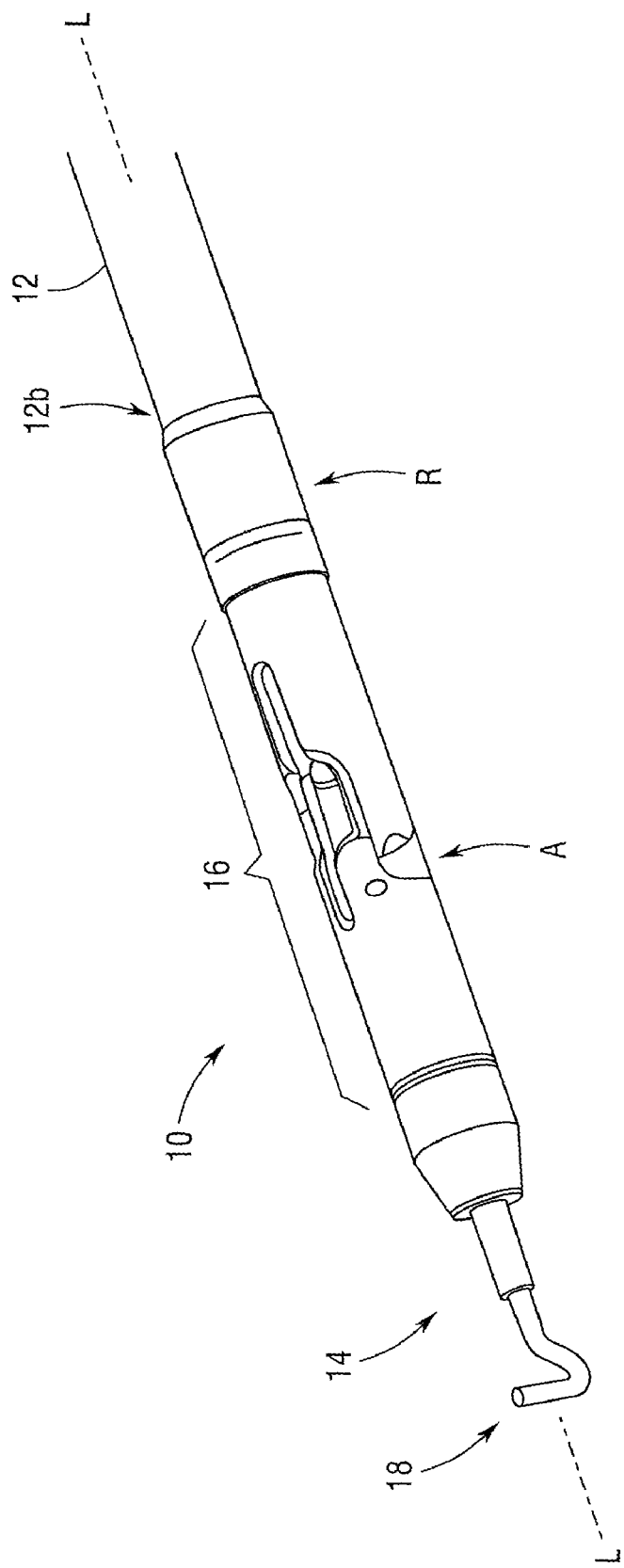
FIG. 1A is a perspective view of a distal end of a surgical device according to one embodiment.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Corresponding reference characters indicate corresponding parts throughout the several views. The exemplifications set out herein illustrate preferred embodiments of the invention, in one form, and such exemplifications are not to be construed as limiting the scope of the invention in any manner.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present application.

The present invention generally provides methods and devices for controlling movement of a working end of a surgical device, and in particular for performing various surgical procedures using an instrument having an end effector that can be articulated relative to an elongate shaft of the device. In certain embodiments, the end effector can also optionally rotate relative to the elongate shaft of the device, and/or the shaft can rotate relative to a handle portion of the device. Articulation and rotation of the end effector will allow the end effector to be positioned at various locations during a surgical procedure, thereby providing the user with precise control over the end effector. A person skilled in the art will appreciate that the present invention has application in endoscopic procedures, laparoscopic procedures, and in conventional open surgical procedures, including robotic-assisted surgery.

Figure 1B:
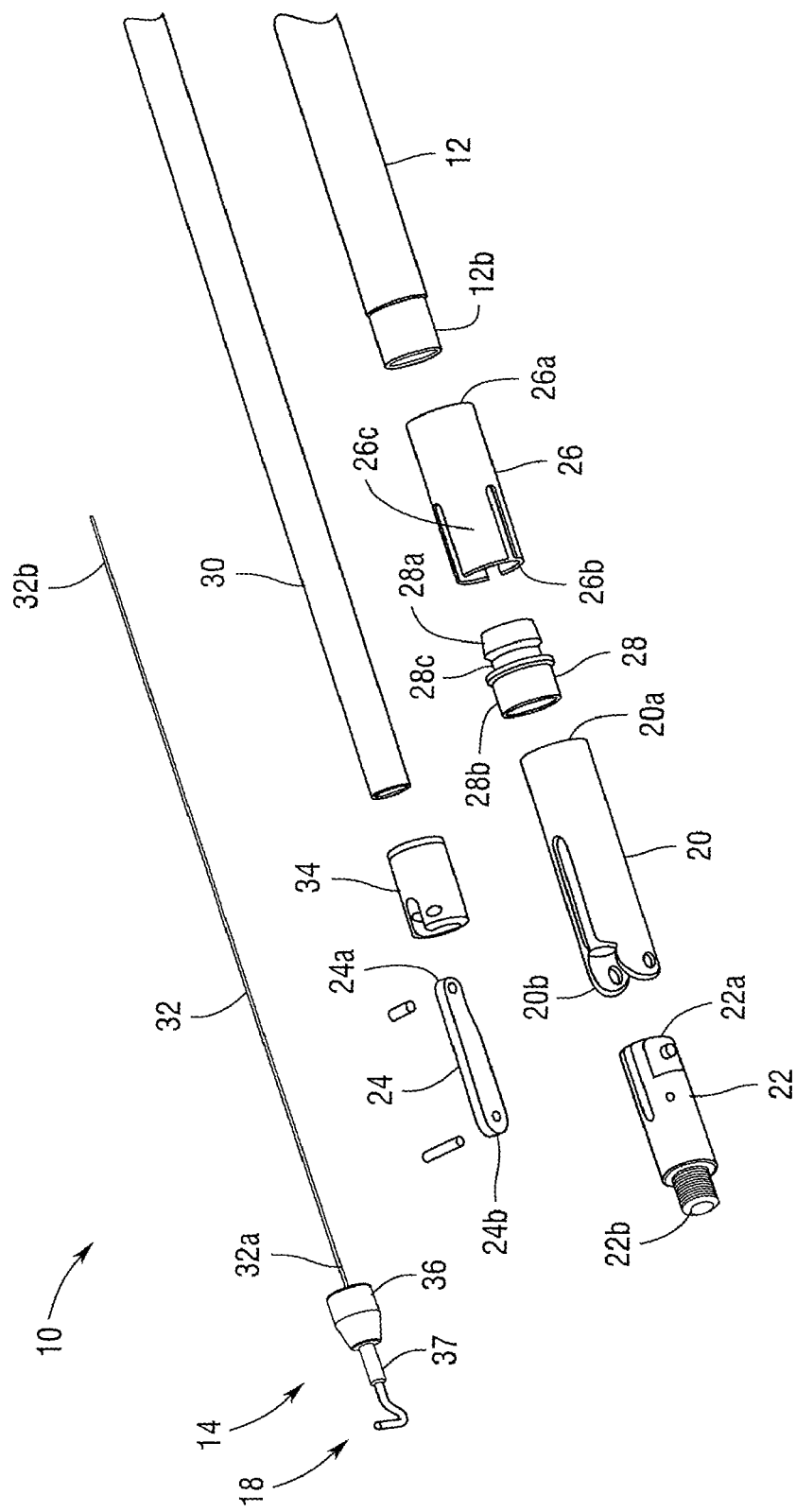
FIG. 1B is a disassembled view of the distal end of the device of FIG. 1A.

FIGS. 1A-1B illustrate one exemplary embodiment of an insertion portion 10 of a manually articulating device. A handle portion 50 of the device will be discussed in more detail below in connection with FIGS. 3A-3D. It will be appreciated that the terms "proximal" and "distal" are used herein with reference to a clinician gripping the handle portion 50 of the device. Thus, the insertion portion 10 is distal with respect to the more proximal handle portion 50. The insertion portion 10 is preferably configured to be inserted into a patient's body, and it can be rigid for laparoscopic applications, flexible for endoscopic applications, or it can have rigid and flexible portions as may be desired. As shown in FIG. 1A, the insertion portion 10 generally includes a hollow elongate shaft 12 having a working end or end effector 14 coupled to a distal end 12b thereof by a three-bar linkage 16. Operation of the three-bar linkage 16 is described in commonly-owned U.S. application Ser. No. 11/610,803 to Nobis et al. entitled MANUALLY ARTICULATING DEVICES, the disclosure of which is incorporated herein by reference it its entirety. While the end effector 14 can have various configurations, in the illustrated embodiment the end effector 14 is configured for use with a hook knife 18. The three-bar linkage 16 allows the end effector 14 to be oriented at an angle relative to a longitudinal axis L of the elongate shaft 12. The device can also optionally be configured to allow the end effector 14 to rotate relative to and about the longitudinal axis L of the elongate shaft 12. In the illustrated embodiment, the three-bar linkage 16 is rotatably coupled to the distal end 12b of the elongate shaft 12, and thus the three-bar linkage 16, as well as the end effector 14 coupled thereto, can be positioned in various axial orientations. The location of the rotation joint R proximal of the articulation joint A is particularly advantageous in that rotation of the end effector 14 can change the location of the plane within which the end effector 14 articulates.

Figure 1C:
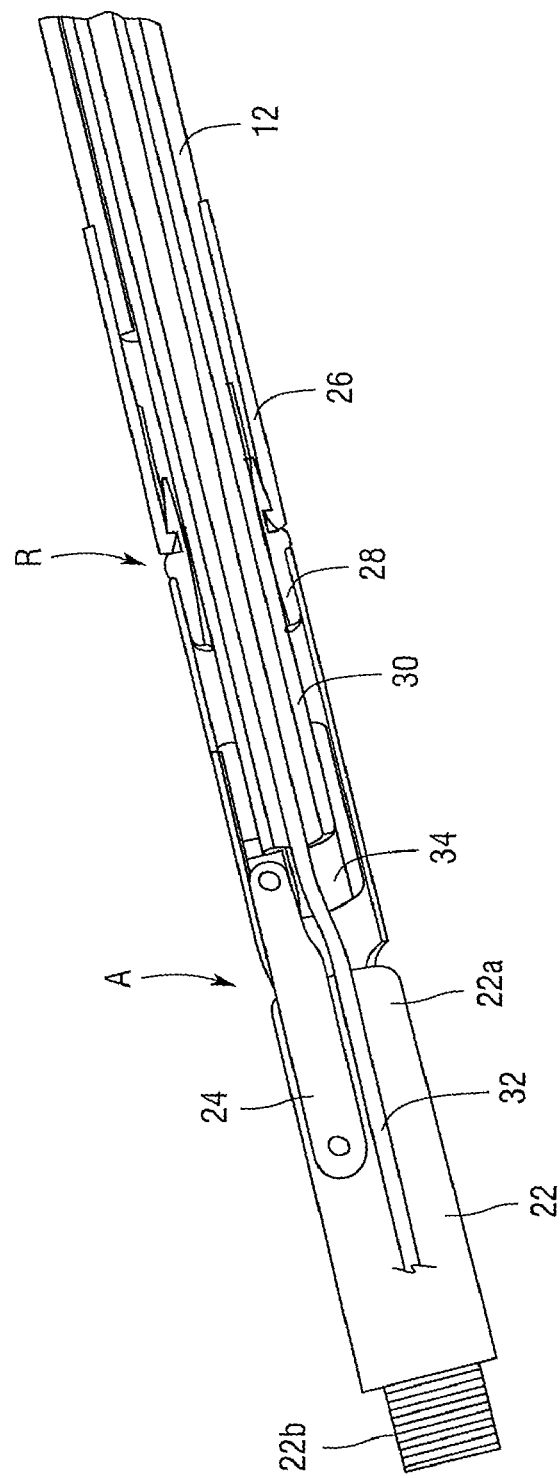
FIG. 1C is a cross-sectional view of the distal end of the device of FIG. 1A.
Figure 1D:
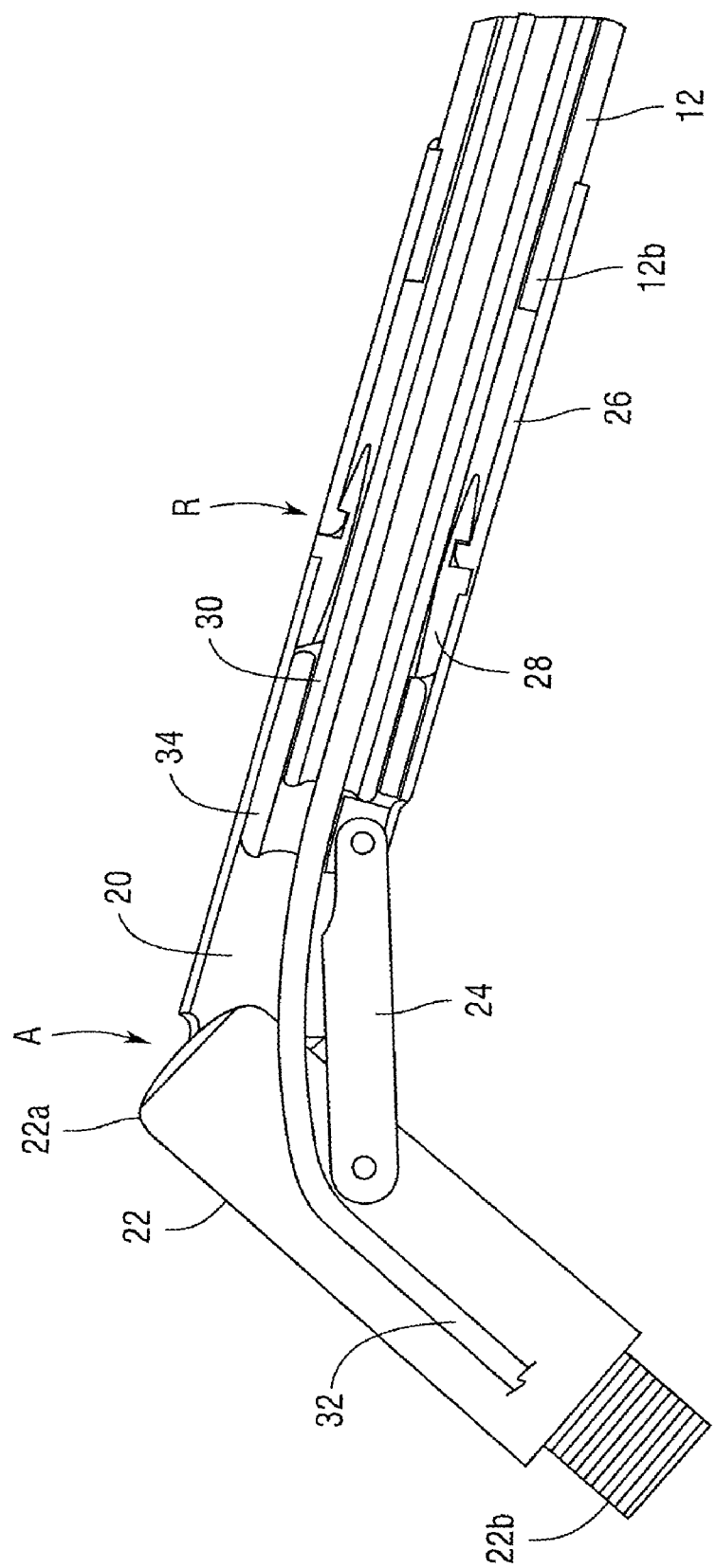
FIG. 1D is a cross-sectional view of the distal end of the device of FIG. 1A in an articulated state.

The three-bar linkage 16 can have a variety of configurations, but in an exemplary embodiment, as shown in more detail in FIGS. 1B-1D, it includes three links 20, 22, 24 that are pivotally coupled to one another. Each link can have a variety of configurations, but in an exemplary embodiment the first and second links 20, 22 each have a generally hollow elongate shape and the third link 24 is in the form of an elongate rod or bar. The first link 20 can have a proximal end 20a that is coupled to the distal end 12b of the elongate shaft 12 via first and second rotation couplings 26, 28, which will be discussed in more detail below. The distal end 20b of the first link 20 can be pivotally coupled to a proximal end 22a of the second link 22, e.g., by a pivot joint. The distal end 22b of the second link 22 can in turn be coupled to the end effector 14, which will be discussed in more detail below. The third link 24 can extend at least partially through the first and second links 20, 22, and it can have a distal end 24b that is pivotally coupled to the second link 22, e.g., by a pivot pin, to form a three-bar linkage mechanism. The particular location at which the third link 24 mates to the second link 22 can vary, but it is preferably pivotally mated at a location that will allow the third link 24 to apply a force to the second link 22 to cause the second link 22 to articulate relative to the first link 20. A proximal end 24a of the third link 24 can be coupled to an articulation actuator 30 extending through the elongate shaft 12 and at least partially through the first link 20. The articulation actuator 30 can have a variety of configurations, but in an exemplary embodiment the articulation actuator 30 is in the form of a hollow elongate shaft or tube. Such a configuration allows an actuation wire 32 to extend therethrough for actuating the end effector 14, as will be discussed below. FIG. 1B also illustrates an articulation coupling 34 for connecting the articulation actuator 30 to the third link 24. The coupling 34 may be a tubular member that fixedly mates to the articulation actuator 30 and pivotally mates to the proximal end 24a of the third link 34. A person skilled in the art will appreciate that the articulation actuator 30 can alternatively be directly mated to the third link 24.

In use, proximal movement of the articulation actuator 30 relative to and along the longitudinal axis L of the elongate shaft 12 will apply a proximally-directed force to the third link 24. The third link 24 will thus apply a proximally-directed force to the second link 22, causing the second link 22 to pivot laterally relative to the longitudinal axis L of the elongate shaft 12. As a result, the second link 22, with the end effector 14 coupled thereto, will move laterally in a single plane to allow the end effector 14 to extend at an angle relative the longitudinal axis L of the elongate shaft 12, as shown in FIG. 1D. The end effector 14 can be returned to the original, longitudinally-aligned position, shown in FIGS. 1A and 1C, by moving the articulation actuator 30 distally relative to the elongate shaft 12.

As previously indicated, in addition to articulating movement, the end effector 14 can also be configured to rotate relative to the elongate shaft 12, thus allowing the end effector 14 to be positioned in multiple angular orientations. The particular location of the rotation joint R can vary, and it can be located proximal to the three-bar linkage 16, at a mid-portion of the three-bar linkage 16, or distal to the three-bar linkage 16. In an exemplary embodiment, the rotation joint R is located proximal to the three-bar linkage 16, and more preferably proximal to the articulation joint A formed between the first and second links 20, 22. As shown in FIGS. 1A-1D, the first link 20 can be rotatably coupled to the distal end 12b of the elongate shaft 12 by one or more rotation couplings. The illustrated embodiment includes first and second rotation couplings 26, 28. The first rotation coupling 26 has a generally elongate hollow shape with a proximal end 26a that is fixedly mated to the elongate shaft 12 and a distal end 26b having deflectable tabs 26c formed therearound. The tabs 26c can be formed by longitudinally-extending cut-outs formed in and spaced radially around the distal end 26b of the first rotation coupling 26. Each tab 26c can include an annular flange or lip (not shown) formed on an inner surface thereof. The second rotation coupling 28 can also have a generally elongate hollow shape, and it can include a groove or cut-out 28c formed therein. The first and second rotation couplings 26, 28 can be mated by advancing the tabs 26c over the proximal end 28a of the second rotation coupling 28. The tabs 26c will deflect until the annular flange or lip on the tabs 26c extends into and engages the groove 28c formed in the second rotation coupling 28. The two rotation couplings 26, 28 can thus rotate relative to one another, allowing the first link 20, which is fixedly mated to the distal end 28b of the second rotation coupling 28, to rotate relative to the first rotation coupling 26 and the elongate shaft 12. It will be appreciated that the particular construction the rotation joint described above is provided by way of example only, and that the function of the rotation joint may be realized using any of a variety of different components.

Rotation of the end effector 14 relative to the elongate shaft 12 can be achieved by rotating the articulation actuator 30. In particular, rotation of articulation actuator 30 relative to and about the longitudinal axis L of the elongate shaft 12 will rotate the third link 24, which is coupled to the second link 22, which in turn is coupled to the end effector 14 and the first link 20. As a result, the entire three-bar linkage 16 will rotate with the end effector 14 relative to and about the longitudinal axis L of the elongate shaft 12. Rotation can also be performed while the end effector 14 is articulated, thereby changing the plane within which the end effector 12 articulates.

Figure 1E:
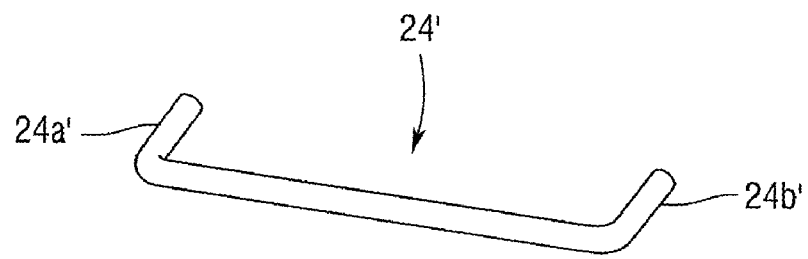
FIG. 1E is a perspective view of a link for use within a distal end of a surgical device according to one embodiment.
Figure 1F:
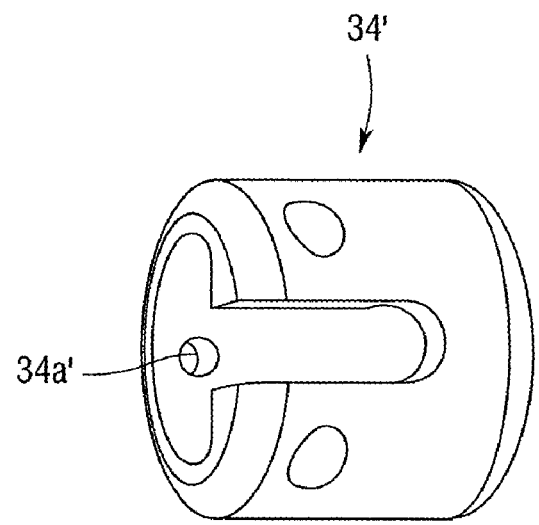
FIG. 1F is a perspective view of an articulating coupling configured for use with the link of FIG. 1E according to one embodiment.

FIGS. 1E-1H illustrate alternative embodiments of a three-bar linkage. In one embodiment, shown in FIGS. 1E-1F, the third link 24 of FIGS. 1B-1D can be replaced with a flexible link. While the flexible link can have a variety of configurations, and it can be in the form of a flexible cable or similar member, FIG. 1E illustrates a flexible wire 24'. As shown, the wire 24' has a generally elongate shape with first and second terminal ends 24a', 24b' that are bent to extend at an angle, e.g., 90°, relative to the remainder of the wire 24'. The ends 24a', 24b' are configured to replace the pivot pins used to pivotally couple the third link 24 to the first and second links 20, 22 of the embodiment shown in FIGS. 1A-1D. Thus, the ends 24a', 24b' can extend into and pivotally couple to the first and second links 20, 22 (FIGS. 1B-1D) to allow the first, second, and third links 20, 22, 24' to pivot relative to one another. In use, proximal movement of the articulation actuator 30 relative to and along the longitudinal axis L of the elongate shaft 12 will apply a proximally-directed force to the third link 24'. The third link 24' will thus flex or buckle, thereby causing the second link 22 to pivot laterally relative to the longitudinal axis L of the elongate shaft 12. As a result, the second link 22, with the end effector 14 coupled thereto, will move laterally in a single plane to allow the end effector 14 to extend at an angle relative the longitudinal axis L of the elongate shaft 12. The end effector 14 can be returned to the original, longitudinally-aligned position, shown in FIGS. 1A and 1C, by releasing the articulation actuator 30 to allow the flexible link 24' to return to its original, non-flexed position shown in FIG. 1E, thereby forcing the articulation actuator 30 to move distally relative to the elongate shaft 12. The flexible link 24' can also be used to transfer rotational forces to effect rotation of the end effector, but in an exemplary embodiment the articulating coupling 34 (FIGS. 1B-1D) is modified to be non-rotatably coupled to the first link 20. As shown in FIG. 1F, which illustrates an alternative embodiment of an articulating coupling 34', this can be achieved by inserting a pin member (not shown) through a bore 34a' formed in the articulating coupling 34', and positioning the pin member such that it is slidably disposed within a longitudinal slot (not shown) formed in the first link 20. As a result, when the articulation actuator 30 is rotated relative to and about the longitudinal axis L of the elongate shaft 12, the articulating coupling 34' will rotate therewith, thereby causing the first and second links 20, 22 to rotate, as well as the end effector 14. As a result, the entire three-bar linkage 16 will rotate with the end effector 14 relative to and about the longitudinal axis L of the elongate shaft 12. Rotation can also be done while the end effector 14 is articulated, thereby changing the plane within which the end effector 12 articulates.

FIGS. 1G-1H illustrate another embodiment of a three-bar linkage that is similar to the three-bar linkage shown in FIGS. 1A-1D. However, in this embodiment a cam 24" replaces both the third link 24 and the articulating coupling 34 of the previous embodiment. As shown in FIG. 1G, the cam 24" is generally hook-shaped and includes a curved slot 24a" formed therein. A proximal end 24p" of the cam 24" can be fixedly mated to the distal end of the articulation actuator 30, and a pin 25" can be slidably disposed through the slot 24a". The pin 25" can be fixedly mated to or formed on an inner wall of the third link 22. As with the embodiment shown in FIGS. 1B-1D, the first and second links 20", 22" can be pivotally coupled to one another. In FIG. 1G, the first link 20" is similar to first link 20 of FIGS. 1B-1D, however link 20" has opposed bores 20a", 20b" spaced a distance apart from the distal end 20d" of the link 20" for receiving opposed pins (only one pin 22b" is shown) formed on the proximal end 22a" of the second link 22". In use, as shown in FIG. 1H, distal movement of the articulation actuator 30 will move the cam 24" distally. As the cam 24" is moved relative to the pin 25", the cam slot 24a" will force the pin 25" to follow the path of the slot 24a". As a result, the second link 22" is caused to pivot laterally relative to a longitudinal axis of the elongate shaft (not shown). As a result, the second link 22", with the end effector (not shown) coupled thereto, will move laterally in a single plane to allow the end effector to extend at an angle relative the longitudinal axis of the elongate shaft. The end effector can be returned to the original, longitudinally-aligned position by moving the articulation actuator 30 proximally and thereby pulling the cam 24" proximally. Again, the cam slot 24a" will cause the pin 25" to slid therein and follow the path of the slot 24a", thus causing the second link 22" to return to its original, longitudinally aligned position.

Figure 2A:
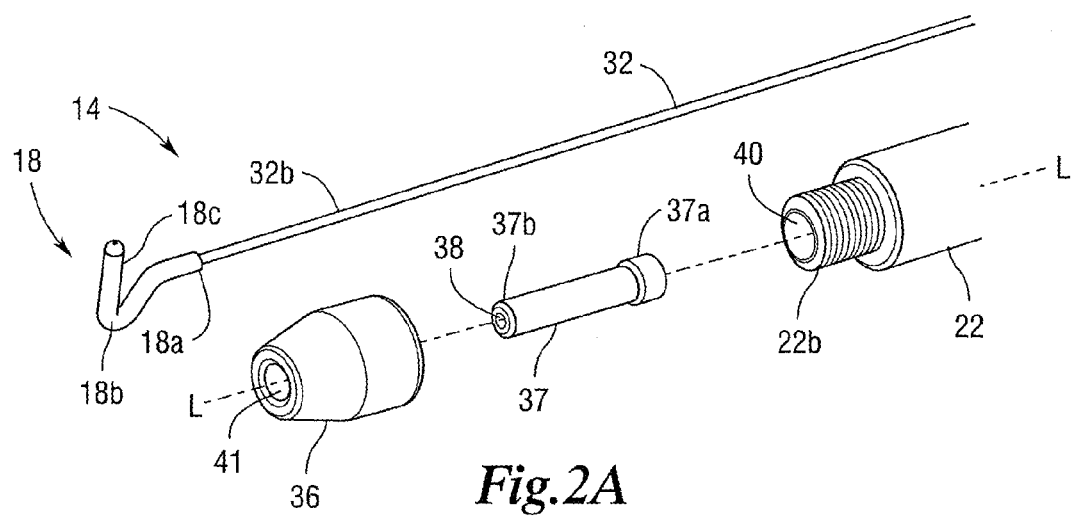
FIG. 2A is a disassembled view of the end effector of FIG. 1A.
Figure 2B:
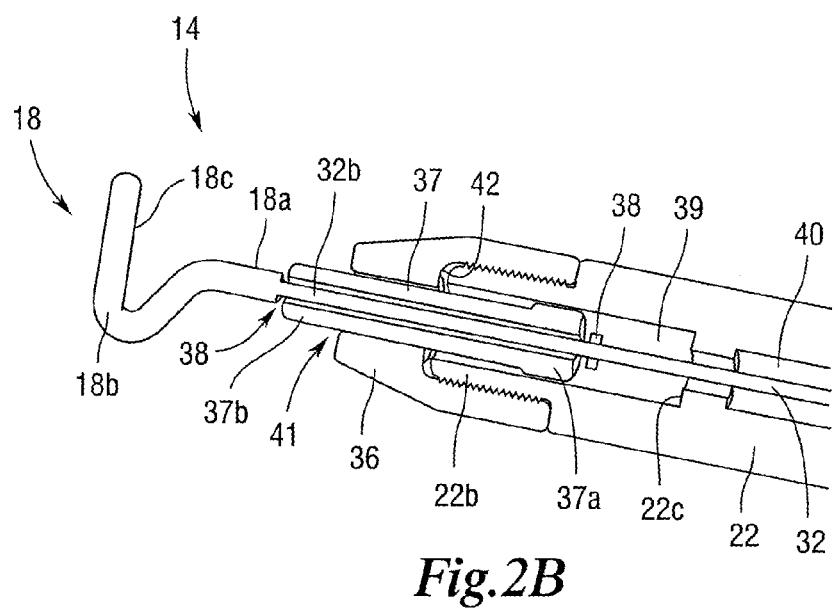
FIG. 2B is a cross-sectional view of the end effector of FIG. 1A.

FIGS. 2A-2B illustrate exploded and cross-sectional views, respectively, of the end effector 14 of FIGS. 1A-1B. Also shown is the distal end 22b of the second link 22 to which the end effector 14 is attached in an assembled state of the device. The end effector 14 may comprise, in addition to the hook knife 18, a distal tip 36, a sleeve 37, and a distal end 32b of the actuating wire 32. The hook knife 18 may be fabricated from a biocompatible material of suitable hardness and durability, such as, for example, medical grade stainless steel, and comprise a generally hook-shaped distal end 18b having a sharpened inner edge 18c formed thereon for cutting tissue when pulled therethrough. A proximal end 18a of the hook knife 18 may be configured for attachment to the distal end 32b of the actuating wire 32 using, for example, a press fit or other suitable attachment technique. In one embodiment, the hook knife 18 may be detachable from the distal end 32b of the actuating wire 32 so that it may be replaced. In another embodiment, the hook knife 18 may be permanently affixed to the distal end 32b.

The sleeve 37 may be generally cylindrical in shape and comprise a longitudinal bore 38 through which the distal end 32b of the actuating wire 32 coaxially extends. As shown in FIG. 2A, a proximal end 37a of the sleeve 37 may comprise an outer diameter larger than that of more distal portions of the sleeve 37 for enabling the proximal end 37a to be slidably retained within the distal end 22b of the second link 22, as discussed in more detail below. The longitudinal position of the sleeve 37 on the actuating wire 32 may be such that a distal end 37b of the sleeve 37 is adjacent, or in contact with, the proximal end 18a of the hook knife 18. In one embodiment, the longitudinal position of the sleeve 37 on the actuating wire 32 may be fixed using, for example, a crimp 38 (FIG. 2B) or other fastening device affixed to the actuating wire 32 adjacent the proximal end 37a of the sleeve 37. Accordingly, the sleeve 37 may be retained on the actuating wire 32 between the proximal end 18a of the hook knife 18 and the crimp 38 such that the actuating wire 32 (and thus the hook knife 18) are independently rotatable relative to a longitudinal axis of the sleeve 37. Alternatively, the longitudinal position of the sleeve 37 on the actuating wire 32 may be fixed using, for example, a suitable adhesive material disposed within the bore 38. In this embodiment, rotation of the actuation wire 32 and hook knife 18 will result in corresponding rotation of the sleeve 37. In one embodiment, the sleeve 37 may be constructed of an electrically non-conductive biocompatible plastic. In other embodiments, the sleeve 37 may be constructed of an electrically non-conductive and suitably heat-resistant biocompatible material, such as, for example, a ceramic material. A heat-resistant construction of the sleeve 37 may be used, for example, in electrosurgical configurations of the device, as discussed in more detail below.

Figure 2C:
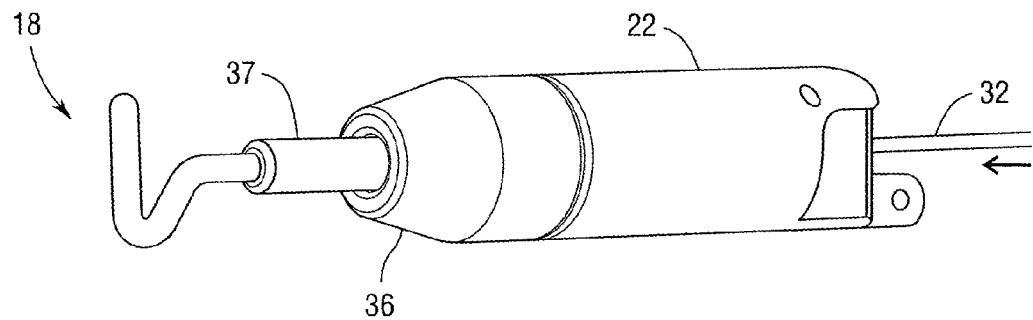
FIGS. 2C-2D illustrates extended and retracted states of the end effector of FIG. 1A according to one embodiment.
Figure 2D:
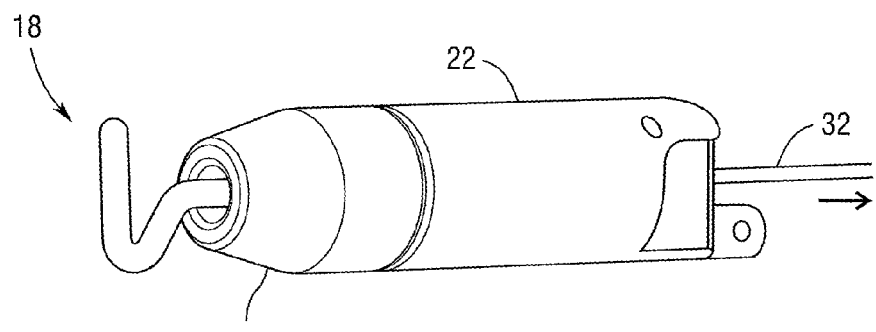

With reference to FIG. 2B, the proximal end 37a of the sleeve 37 may be slidably disposed within a recess 39 defined by the distal end 22b of the second link 22. As shown, the recess 39 may form the distal-most portion of a bore 40 extending longitudinally through the second link 22. The distal end 37b of the sleeve 37 may distally protrude from the recess 39 and pass through a longitudinal bore 41 defined by the distal tip 36. The distal tip 36 may be longitudinally aligned with and coupled to the distal end 22b of the second link 22 such that a proximally-facing surface 42 formed by a restriction of the bore 41 partially encloses the recess 39 at its distal end. The distal tip 36 may be coupled to the distal end 22b using, for example, a threaded connection or other suitable connection technique. Distal movement of the sleeve 37 relative to the distal tip 36 is thus limited by engagement of the outer diameter of the proximal end 37a of the sleeve 37 by the proximally-facing surface 42 of the distal tip 36. Similarly, proximal movement of the sleeve 37 relative to the distal tip 36 is limited by engagement of the outer diameter of the proximal end 37a of the sleeve 37 by a surface 22c at a proximal end of the recess 39. Distal and proximal movement of the actuating wire 32 (FIGS. 2C-2D, respectively) therefore results in a corresponding extension and retraction of the hook knife 18 relative to the distal tip 36, as well as a corresponding telescopic extension and retraction of a portion of the sleeve 37 relative to the distal tip 36. The amount of the extension and retraction is limited by the degree of longitudinal movement of the proximal end 37a of the sleeve 37 within the recess 39 (FIG. 2B). Additionally, because the actuation wire 32 may be rotated independently about its longitudinal axis relative to the longitudinal axis of the distal tip 36 (e.g., by rotating the actuation wire 32 within the sleeve 37 or by rotating the actuation wire 32 and the sleeve 37 together within the recess 39 of the second link 22), the hook knife 18 may be rotationally positionable relative to the longitudinal axis of the distal tip 36. As discussed below, distal, proximal and rotational movement of the actuating wire 32 relative to the distal tip 36 may be controlled via the handle portion 50 of the device.

Figure 3A:
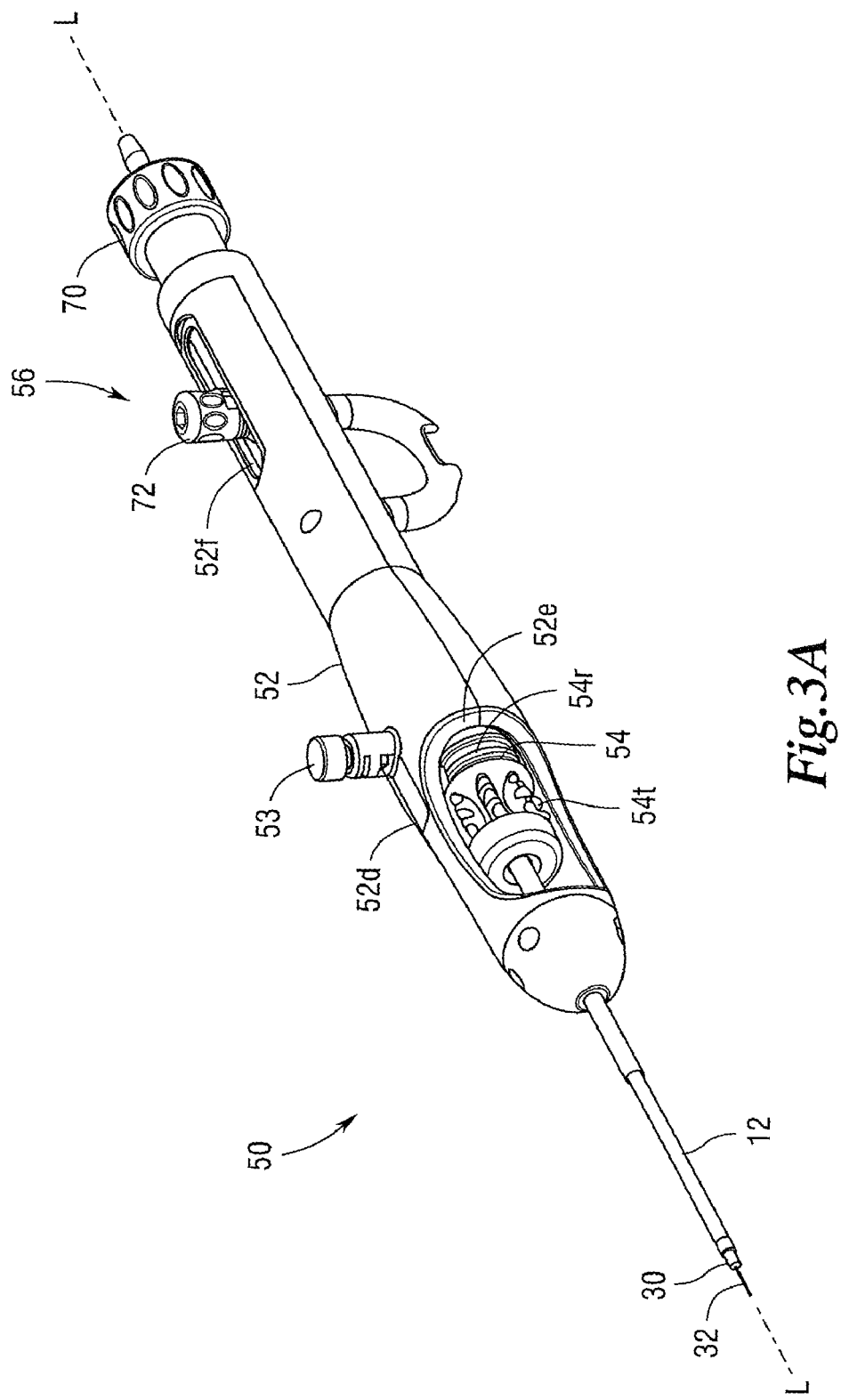
FIG. 3A is a perspective view of a handle portion of a surgical device according to one embodiment.
Figure 3B:
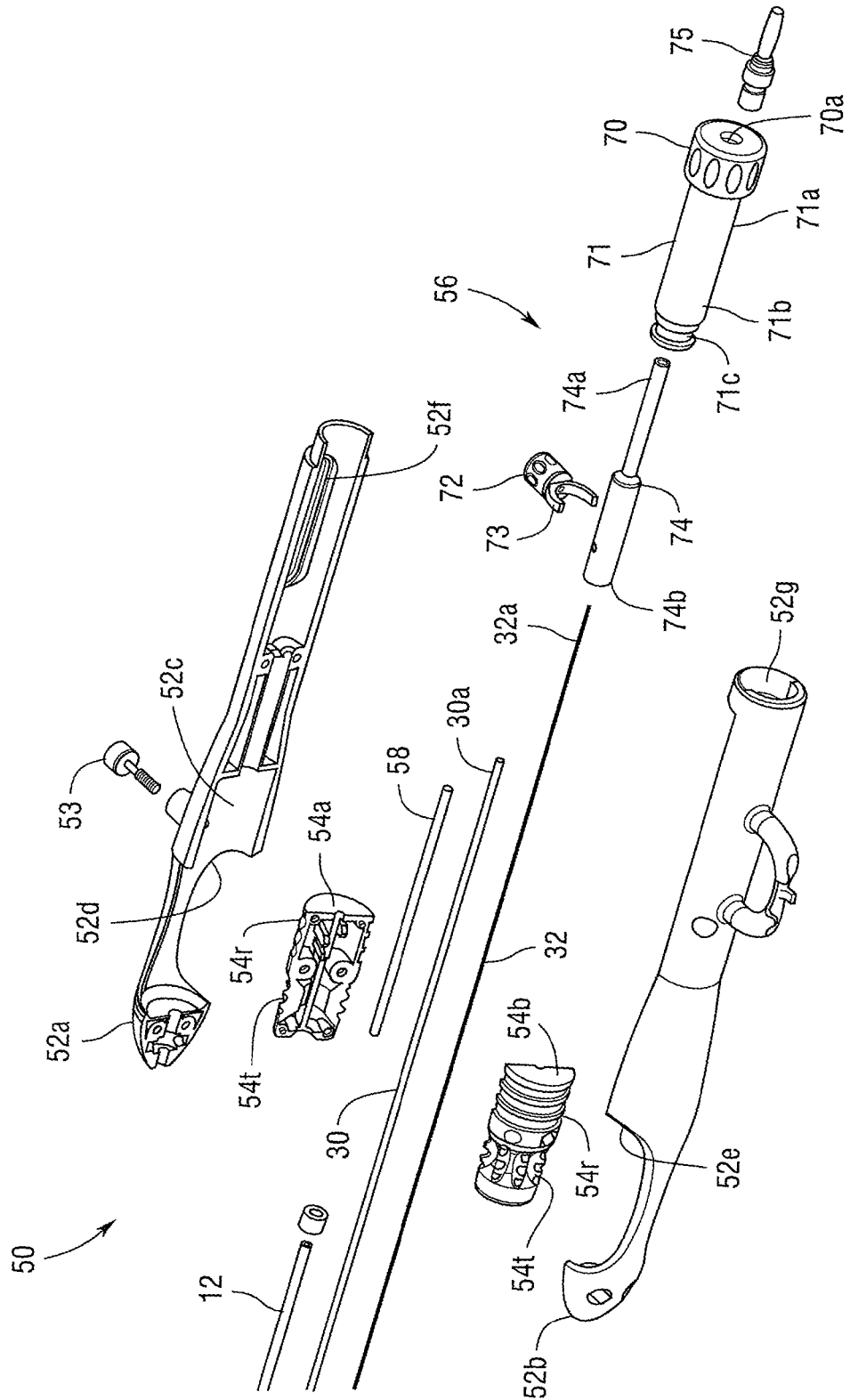
FIG. 3B is an exploded view of the handle portion of FIG. 3A.

As previously indicated, the device can also include a handle portion coupled to the proximal end of the elongate shaft and having various controls formed thereon for controlling and manipulating the device. A person skilled in the art will appreciate that the particular configuration of the handle portion can vary, and that various techniques known in the art can be used for effecting movement of various portions on the device. FIGS. 3A-3D illustrate one exemplary embodiment of a handle portion 50 for use with the insertion portion 10 of the device shown in FIG. 1A. As shown in FIG. 3A, the handle portion 50 has a generally elongate cylindrical configuration to facilitate grasping thereof. The handle housing 52 can have an integral or unitary configuration, or it can be formed from two housing halves 52a, 52b that mate to enclose various components therein. The housing halves 52a, 52b are shown in FIG. 3B. The various component disposed within the handle housing 52 can also vary, but in an exemplary embodiment the handle portion 50 includes a first knob 54 for articulating and rotating the end effector 14, and an actuation controller 56 for actuating the end effector 14.

Figure 3C:
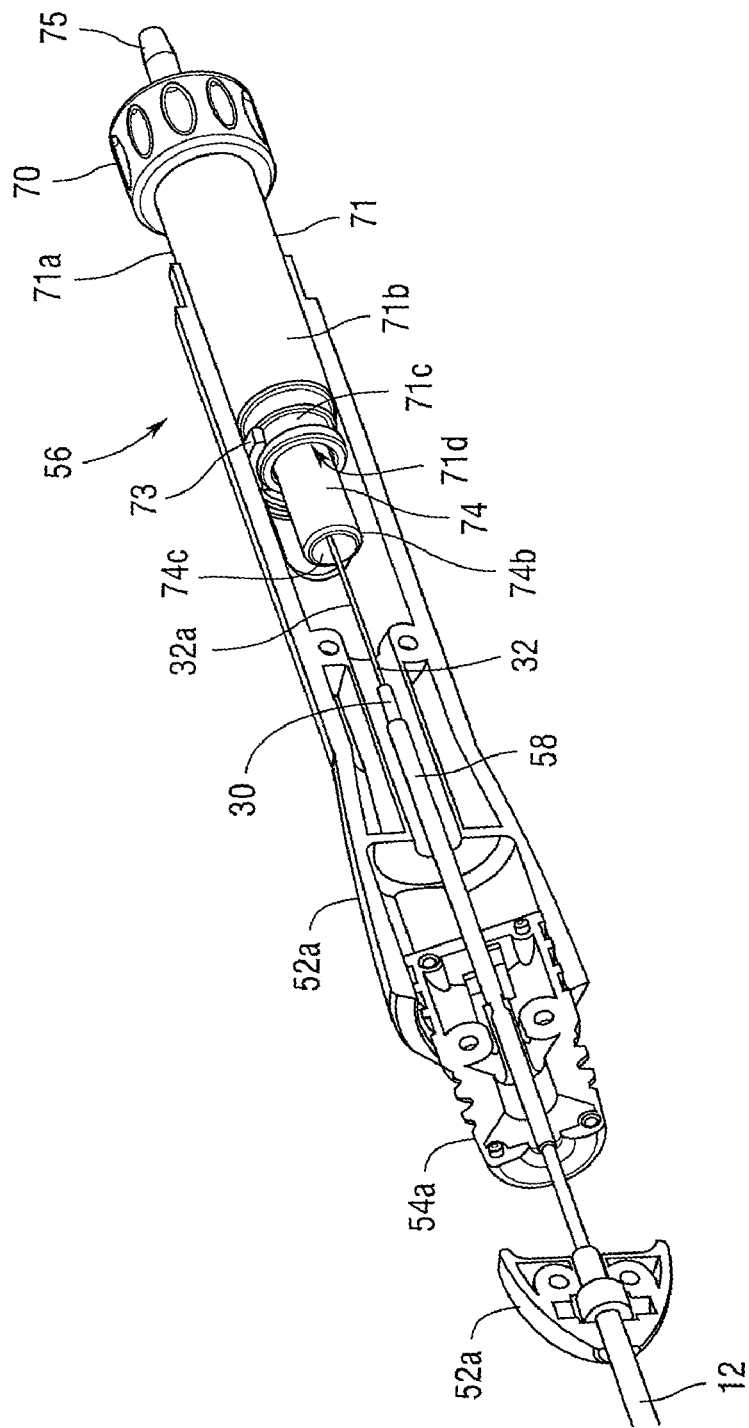
FIG. 3C is a cross-sectional view of the handle portion of FIG. 3A.

The first knob 54 is shown in more detail in FIGS. 3B and 3C, and as shown the first knob 54 has a generally cylindrical configuration. The first knob 54 can have an integral or unitary configuration, or it can be formed from two halves 54a, 54b that mate together, as shown. A proximal end 30a of the articulation actuator 30 can mate to the first knob 54 such that rotation and translation of the first knob 54 will cause corresponding rotation and translation of the articulation actuator 30, thereby rotating and articulating the end effector 14, as previously described. While various techniques can be used to mate the articulation actuator 30 to the first knob 54, in an exemplary embodiment the articulation first knob 54 includes an axle 58 fixedly disposed therein and engaged between the knob halves 54a, 54b. The articulation actuator 30 extends through an inner lumen of the axel 58 and is fixedly mated thereto. Various mating techniques can be used to mate the articulation actuator 30 to the axel 58 including, for example, an interference or compression fit, an adhesive, or other mechanical or chemical mating techniques known in the art.

In order to translate and rotate the first knob 54, the handle housing 52 can include an elongate cavity 52c (FIG. 3B) formed therein that slidably and rotatably receives the first knob 54. The handle housing 52 can also include one or more cut-outs formed therein for allowing a user to access the first knob 54. FIGS. 3A-3B illustrate opposed cut-outs 52d, 52e formed in the handle housing 52. The first knob 54 can also include features to facilitate movement thereof. For example, the first knob 54 can include one or more surface features formed on an external surface thereof for allowing the user to more easily grasp the first knob 54. In the illustrated embodiment, the first knob 54 includes a series of ridges 54r formed therein, as well as a series of longitudinally-oriented teeth 54t formed on a portion thereof. In one embodiment, the ridges 54r may be selectively engaged by a thumb screw 53 accessible from the exterior of the handle housing 52 such that the articulation and rotational positions may be selectively maintained. In another embodiment, the ridges 54r can provide a detent feature to maintain the position of the articulation. A corresponding detent snap can be located in the cavity 52c.

In use, the first knob 54 can be grasped by a user and rotated about its longitudinal axis (i.e., about the longitudinal axis L of the shaft 12 and handle portion 50). Rotation of the knob will cause corresponding rotation of the axel 58 and the articulation actuator 30. The actuation wire 32, which extends through the articulation actuator 30, will not rotate with the articulation actuator 30 since it is not coupled thereto. As previously explained, rotation of the articulation actuator 30 will cause corresponding rotation of the three-bar linkage 16 and the end effector 14 coupled thereto. The first knob 54 can also be slid or translated longitudinally along its axis L, and within the elongate cavity 52c formed in the handle housing 52. Proximal movement of the first knob 54 within the handle housing 52 will pull the articulation actuator 30 proximally, thereby articulating the end effector 14, as previously explained. Distal movement of the first articulation knob 54 within the handle housing 52 will in turn move the articulation actuator 30 distally, thereby returning the end effector 14 to its original longitudinally-aligned position.

As indicated above, the handle portion 50 can also include an actuation controller 56 for actuating the end effector 14 (e.g., extending, retracting and/or rotating the hook knife 18 relative to the distal tip 36). The actuation controller 56 can have a variety of configurations, but in the illustrated embodiment the actuation controller 56 comprises a second knob 70 attached to a proximal end 71a of a rotation tube 71 that is slidably disposed through a distal opening 52g formed in the handle housing 52. The second knob 70 may generally form the proximal end of the handle portion 50. Longitudinal movement of the second knob 70 along the longitudinal axis of the handle housing 52 causes corresponding longitudinal movement of the rotation tube 71 within the handle housing 52. Similarly, rotational movement of the second knob 70 about the longitudinal axis of the handle housing 52 causes corresponding rotational movement of the rotation tube 71 within the handle housing 52.

The actuation controller 56 may also include a third knob 72 accessible from the exterior of the handle housing 52 and longitudinally slidable relative to the handle housing 52 via a slot 52f formed therein. The third knob 72 may be coupled to a yolk 73 (FIGS. 3B-3C) that extends from the third knob 72 into the interior of the handle housing 52. The yolk 73 may be received through a circumferential slot 71c formed on a distal end 71b of the rotation tube 71. Because the yolk 73 is received through the circumferential slot 71c of the rotation tube 71, longitudinal movement of the rotation tube 71 via the second knob 70 causes corresponding longitudinal movement of the yolk 73, and, therefore, corresponding longitudinal movement of the third knob 72, relative to the slot 52f. Because the yolk 73 is not otherwise attached to the rotation tube 71, the yolk 73 does not prevent rotational movement of the rotation tube 71 via the second knob 70.

In one embodiment, the third knob 72 may be threadingly coupled to the yolk 73 such that the third knob 72 is selectively tightenable and untightenable relative to the yolk 73. In a tightened, or "locked", state of the third knob 72, a base 72a (FIG. 3D) of the third knob 72 may be pushed into contact with an adjacent outer perimeter of the slot 52f, thereby causing an opposing portion of the yolk 73 to be pulled into contact with an adjacent inner perimeter of the slot 52f. In this way, a portion of the handle housing 52 may be clamped between the third knob 72 and the yolk 73 such that the rotation tube 71 is immovably fixed, or locked, into position relative to the longitudinal axis of the handle housing 52. In an untightened, or "unlocked", state of the third knob 72, the base 72a of the third knob 72 may no longer be pushed into contact with the outer perimeter of the slot 52f, in which case the handle housing 52 is no longer clamped between the third knob 72 and the yolk 73. Accordingly, the rotation tube 71 is freely movable along the longitudinal axis of the handle housing 52 using the second knob 70. As noted above, because the yolk 73 is received through the slot 71c of the rotation tube 71 and is not otherwise attached thereto, the rotation tube 71 remains rotatable irrespective of the locked or unlocked state of the third knob 72.

Figure 3D:
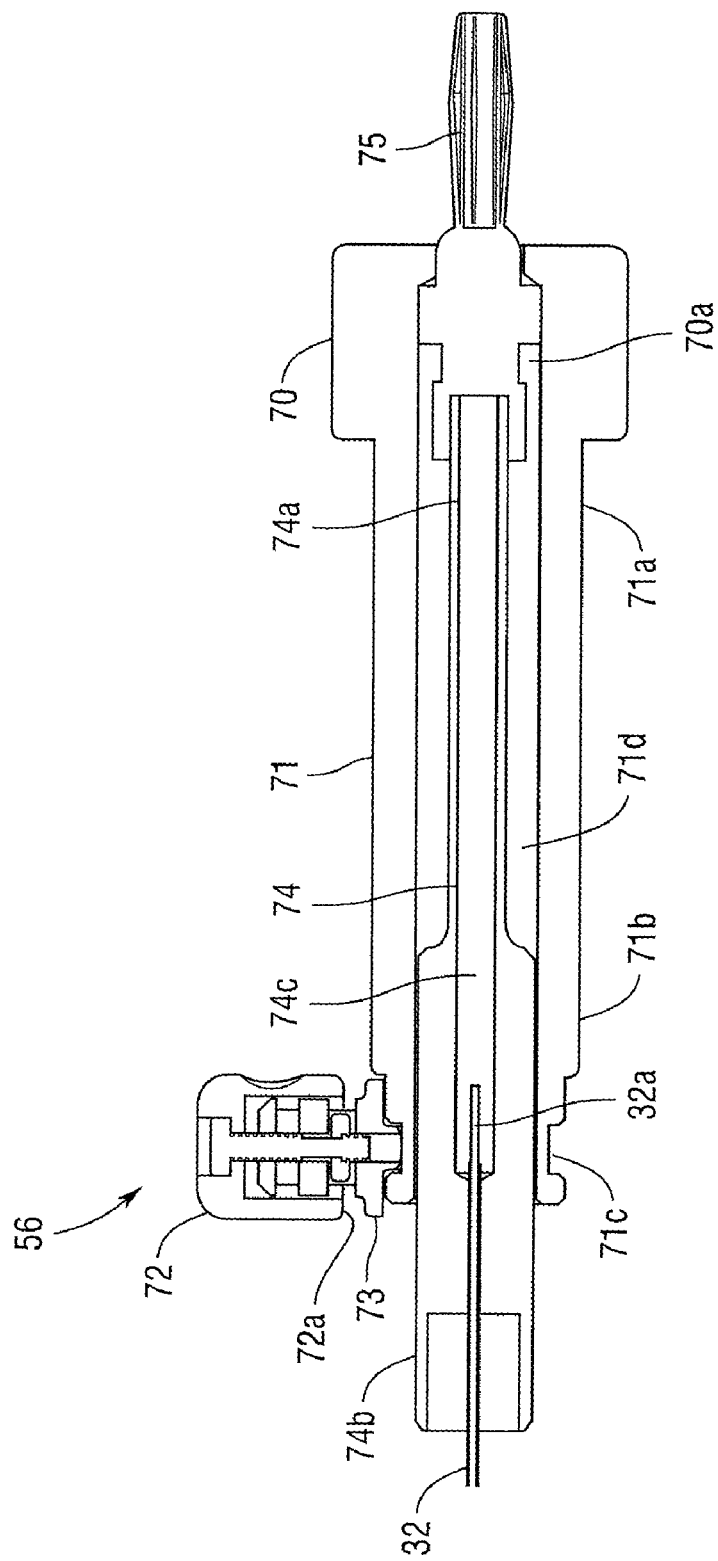
FIG. 3D is a cross-sectional view of the actuation controller of FIG. 3A.

In addition to the second and third knobs 70, 72, the rotation tube 71, and the yolk 73, the actuation controller 56 may further comprise a shaft 74, at least a portion of which is coaxially disposed within a bore 71d defined by the rotation tube 71. According to one embodiment and as shown in FIGS. 3C-3D, the shaft 74 may define a longitudinal bore 74c through which the proximal end 32a of the actuation wire 32 may partially extend. The proximal end 32a of the actuation wire 32 may be retained within the bore 74c using, for example, one or more set screws (not shown) transversely extending into the bore 74c from an exterior surface of the shaft 74 to engage the distal end 32b. A proximal end 74a of the shaft 74 may comprise a reduced outer diameter, with the proximal end 74a aligned with and adjacent an opening 70a formed through the second knob 70. As shown in FIG. 3D, a connector 75 may extend through the opening 70a and into the bore 71d of the rotation tube 71 to engage an inner surface of the opening 70a and the distal end 74a of the shaft 74, thus maintaining the position of the shaft 74 relative to the rotation tube 71. In certain embodiments, the shaft 74 may be constructed from an electrically conductive material (e.g., stainless steel), and the connector 75 may comprise an electrical connector (e.g., a male banana plug connector 75 as shown) that is accessible from the exterior of the handle portion 50. An electrical path may thus be established between the connector 75 and the hook knife 18 via the shaft 74 and the actuation wire 32, and, as discussed in further detail below, the hook knife 18 may be used for electrosurgical procedures by connecting to the connector 75 to a suitable source of electrical energy.

In use, the second knob 70 can be grasped by a user and, with the third knob 72 in an unlocked state, slidably manipulated through the opening 52g of the handle housing 52 along the longitudinal axis of the handle housing 52. Movement of the second knob 70 in the distal direction will cause the rotation tube 71 and the shaft 74, and thus the actuation wire 32, to be correspondingly moved in the distal direction. As discussed above in connection with FIGS. 2C-2D, this results in an extension of the hook knife 18, and a corresponding telescopic extension of a portion of the sleeve 37, relative to the distal tip 36. In the same way, movement of the second knob 70 in the proximal direction will result in a retraction of the hook knife 18, and a corresponding telescopic retraction of a portion of the sleeve 37, relative to the distal tip 36. Generally, the second knob 70 may be used to provide any degree of extension/retraction of the hook knife 18 and sleeve 37 between their fully extended and fully retracted positions. Additionally, subsequent to achieving a desired extended/retracted position of the hook knife 18 and the sleeve 37, the position may be maintained by tightening the third knob 72 relative to the yolk 73, as discussed above.

Additionally, the rotational position of the rotation tube 71 and the shaft 74 relative to the handle portion 52, and thus the rotational position of the actuation wire 32 about the longitudinal axis of the distal tip 36, may be controlled by rotating the second knob 70 about the longitudinal axis of the handle portion 50. In this way, the rotational position of the hook knife 18 relative to the distal tip 18 may be controlled via the second knob 70.

Figure 4:
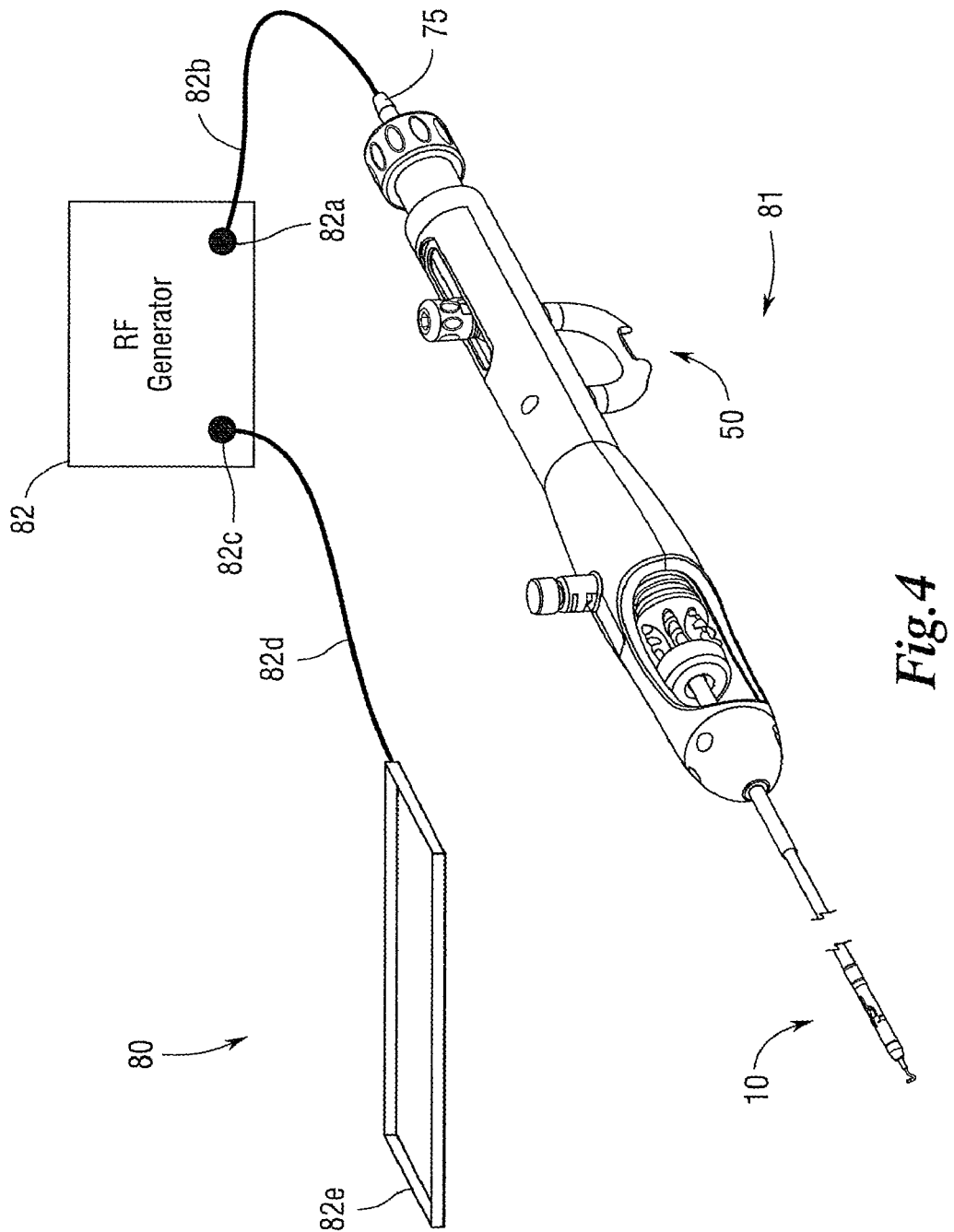
FIG. 4 illustrates a system according to one embodiment.

In certain embodiments and as previously mentioned, the end effector 14 may be suitable for use in electrosurgical procedures by virtue of a conductive path formed between the hook knife 18 and the connector 75 of the handle portion 50. FIG. 4 illustrates a system 80 for performing electrosurgical procedures according to one embodiment. The system may comprise a manually articulating surgical device 81 comprising an insertion portion 10 and a handle portion 50 as described above wherein the hook knife 18 is electrically coupled to the connector 75 (e.g., a male banana connector) via the shaft 74 and the actuation wire 32. To ensure that the articulation wire 32 is suitably insulated from other components within the device 81, electrical insulation (e.g., plastic tubing or an insulative coating) may cover at least a portion of the actuation wire 32. The system 80 may further comprise an energy source 82 comprising a first output 82a electrically coupled to the connector 75 via a first wire 82b, and a second output 82c electrically coupled to a patient to be treated (not shown) via a second wire 82d and a grounding pad 82e. It will be appreciated that this configuration of the system 80 corresponds to a monopolar mode of operation. In one embodiment and as shown, the energy source 82 may comprise a radio frequency (RF) generator to produce RF waveforms at predetermined frequencies, amplitudes, polarities, and pulse widths. The RF generator may be a conventional bipolar/monopolar electrosurgical generator such as one of many models commercially available, including Model Number ICC 350, available from Erbe, GmbH. In use, the insertion portion 10 of the device 81 may be introduced into the patient (e.g., via a flexible endoscope) such that the hook knife 18 of the end effector 14 is adjacent a surgical site comprising an area of tissue. RF energy may be introduced to the tissue by suitably contacting the tissue with the hook knife 18. It will appreciated that RF energy may operate to enhance the cutting ability of the hook knife 14 and/or to perform other electrosurgical procedures, such as, for example, fulguration and desiccation. As discussed above, the sleeve 37 may be fabricated from a heat-resistant material (e.g., a ceramic material) in order to insulate and protect the distal tip 36 from potentially damaging heat dissipated by the hook knife 18 during an electrosurgical procedure.

As indicated above, the various devices disclosed herein for controlling movement of a working end of a surgical device can be used in a variety of surgical procedures, including endoscopic procedures, laparoscopic procedures, and in conventional open surgical procedures, including robotic-assisted surgery. In one exemplary endoscopic procedure, an elongate shaft of a surgical device, such as one previously disclosed herein, can be inserted through a natural orifice and a body lumen to position an end effector located at a distal end of the elongate shaft adjacent to tissue to be treated. An articulation actuator can be translated along a longitudinal axis of the elongate shaft to cause a three-bar linkage to laterally articulate the end effector in a direction substantially perpendicular to a longitudinal axis of the elongate shaft to allow the end effector to be angularly oriented relative to the elongate shaft. This can be achieved by actuating one or more articulation mechanisms formed on a handle of the device. The method can also include rotating the end effector relative to the elongate shaft. In one embodiment, the three-bar linkage can rotate with the end effector relative to the elongate shaft. For example, the articulation actuator can be rotated relative to the elongate shaft to rotate both the three-bar linkage and the end effector. In another embodiment, the end effector can rotate relative to the three-bar linkage. For example, an actuation wire coupled to the end effector and extending through the elongate shaft and the three-bar linkage can be rotated. Once the end effector is suitably positioned, the end effector may be actuated using one or more actuation mechanisms formed on the handle of the device.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

It is to be understood that the figures and descriptions of the present application have been simplified to illustrate elements that are relevant for a clear understanding of the disclosed subject matter. Those of ordinary skill in the art will recognize that these and other elements may be desirable. However, because such elements are well known in the art and because they do not facilitate a better understanding of the present application, a discussion of such elements is not provided herein.

While several embodiments have been described, it should be apparent that various modifications, alterations and adaptations to those embodiments may occur to persons skilled in the art with the attainment of some or all of the advantages disclosed in the present application. It is therefore intended to cover all such modifications, alterations and adaptations without departing from the scope and spirit of the present application as defined by the appended claims.

What is claimed is:

1. A surgical device, comprising:
   an elongate shaft comprising proximal and distal ends;
   an articulation joint comprising proximal and distal ends, the proximal end coupled to the distal end of the elongate shaft, wherein the proximal end of the articulation joint is rotatably coupled to the distal end of the elongate shaft;
   an articulation actuator extending through the elongate shaft and coupled to the articulation joint, wherein the articulation actuator is translatable along the longitudinal axis of the elongate shaft to articulate the articulation joint, wherein the articulation actuator is rotatable within the elongate shaft to rotate the articulation joint about the longitudinal axis of the elongate shaft, wherein the rotation of the articulation joint about the longitudinal axis is independent of an articulation action of the articulation joint, and wherein the articulation actuator comprises a hollow elongate tube;
   an actuation wire extending through the elongate shaft, the articulation actuator, and the articulation joint, wherein the rotation and translation of the actuation wire are independent of rotation and translation of the articulation actuator; and
   an end effector, comprising:
      a distal tip coupled to the distal end of the articulation joint, the distal tip receiving therethrough a distal end of the actuation wire;
      a hook knife disposed adjacent the distal tip and comprising proximal and distal ends, the proximal end of the hook knife attached to the distal end of the actuation wire;
   wherein the actuation wire is translatable along a longitudinal axis of the elongate shaft to extend and retract the distal end of the hook knife relative to the distal tip; and
   wherein the articulation joint is articulatable relative to the longitudinal axis of the elongate shaft to allow the end effector to be angularly oriented relative to the elongate shaft.

2. The device of claim 1, comprising an insulating sleeve rotatably disposed on the distal end of the actuation wire in a position adjacent the proximal end of the hook knife, wherein extension and retraction of the distal end of the hook knife relative to the distal tip causes a corresponding telescopic extension and retraction of the sleeve relative to the distal tip.

3. The device of claim 1, wherein the actuation wire is rotatable about the longitudinal axis of the elongate shaft to rotate the distal end of the hook knife relative to the distal tip.

4. The device of claim 1, wherein the articulation joint comprises:
- a first articulating link comprising a proximal end coupled to the distal end of the elongate shaft;
- a second articulating link comprising a proximal end pivotally coupled to a distal end of the first articulating link, and a distal end coupled to the distal tip of the end effector; and
- a third articulating link comprising a proximal end pivotally coupled to the articulation actuator, and a distal end pivotally coupled to the second articulating link.

5. The device of claim 1, comprising a handle coupled to the proximal end of the elongate shaft, the handle comprising:
- a first knob coupled to the articulation actuator, the first knob to at least one of translate and rotate the articulation actuator relative to the longitudinal axis of the elongate shaft; and
- a second knob coupled to the actuation wire, the second knob to at least one of translate the actuation wire relative to the longitudinal axis of the elongate shaft and rotate the actuation wire about the longitudinal axis of the elongate shaft.

6. The device of claim 5, wherein the handle comprises a third knob for fixing the longitudinal position of the actuation wire relative to the longitudinal axis of the elongate shaft.

7. The device of claim 6, wherein the second knob and the third knob are coupled to the actuation wire via a common shaft.

8. The device of claim 5, wherein the handle is electrically coupled to the hook knife via the actuation wire, and wherein the handle comprises an electrical connector for coupling the hook knife to a source of electrical energy.

9. The device of claim 1, wherein the elongate shaft is flexible.

10. A method for processing the device of claim 1 for surgery, comprising:
- providing the device of claim 1;
- sterilizing the device; and
- storing the device in a sterile container.

* * * * *

UNITED STATES PATENT AND TRADEMARK OFFICE
CERTIFICATE OF CORRECTION

| | | |
|---|---|---|
| PATENT NO. | : 8,403,926 B2 | Page 1 of 1 |
| APPLICATION NO. | : 12/133953 | |
| DATED | : March 26, 2013 | |
| INVENTOR(S) | : Nobis et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1242 days.

Signed and Sealed this
Seventh Day of October, 2014

Michelle K. Lee
*Deputy Director of the United States Patent and Trademark Office*